(12) United States Patent
Amin et al.

(10) Patent No.: US 12,185,630 B2
(45) Date of Patent: Dec. 31, 2024

(54) LAYERED SENSOR HAVING MULTIPLE LATERALLY ADJACENT SUBSTRATES IN A SINGLE LAYER

(71) Applicant: Apple Inc., Cupertino, CA (US)

(72) Inventors: Ali M. Amin, Cupertino, CA (US); Yindar Chuo, Milpitas, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 1037 days.

(21) Appl. No.: 16/929,731

(22) Filed: Jul. 15, 2020

(65) Prior Publication Data

US 2021/0038092 A1 Feb. 11, 2021

Related U.S. Application Data

(60) Provisional application No. 62/891,195, filed on Aug. 23, 2019, provisional application No. 62/885,028, filed on Aug. 9, 2019.

(51) Int. Cl.
*H10N 30/06* (2023.01)
*A61B 5/00* (2006.01)
(Continued)

(52) U.S. Cl.
CPC ........... *H10N 30/06* (2023.02); *A61B 5/0205* (2013.01); *A61B 5/0803* (2013.01); *A61B 5/4809* (2013.01); *A61B 5/6892* (2013.01); *A61B 7/003* (2013.01); *G01H 11/08* (2013.01); *G01L 1/16* (2013.01); *H10N 30/073* (2023.02); *H10N 30/088* (2023.02); *H10N 30/302* (2023.02);
(Continued)

(58) Field of Classification Search
CPC ... A61B 5/4806; A61B 5/4809; A61B 5/6891; A61B 5/6892; A61B 5/024; A61B 5/08; A61B 2562/04; A61B 2562/12; A61B 2562/164; A61B 2562/0247; A61B 2562/0252; A61B 2562/0261; H10N 30/06
See application file for complete search history.

(56) References Cited

U.S. PATENT DOCUMENTS 3,209,380 A 10/1965 Benjamin
3,613,671 A 10/1971 Poor et al.
(Continued)

FOREIGN PATENT DOCUMENTS

CN 104662800 5/2015
CN 205091721 3/2016
(Continued)

OTHER PUBLICATIONS

U.S. Appl. No. 17/339,738, filed Jun. 4, 2021, Tadele et al.
(Continued)

*Primary Examiner* — Devin B Henson
(74) *Attorney, Agent, or Firm* — Brownstein Hyatt Farber Schreck, LLP

(57) ABSTRACT

A sleep monitor includes a layered sensor that includes at least one substrate layer that includes multiple laterally adjacent substrates. The substrate layer may be formed by interdigitating fingers of a first sheet with fingers of a second sheet. Combining multiple substrates in a single layer of a layered sensor may allow multiple materials and/or sensing mechanisms to be combined together in a single layer.

21 Claims, 26 Drawing Sheets

(51) Int. Cl.

| | | |
|---|---|---|
| *A61B 5/0205* | (2006.01) | |
| *A61B 5/024* | (2006.01) | |
| *A61B 5/08* | (2006.01) | |
| *A61B 7/00* | (2006.01) | |
| *G01H 11/08* | (2006.01) | |
| *G01L 1/16* | (2006.01) | |
| *H10N 30/073* | (2023.01) | |
| *H10N 30/088* | (2023.01) | |
| *H10N 30/30* | (2023.01) | |
| *H10N 30/857* | (2023.01) | |
| *H10N 30/87* | (2023.01) | |
| *H10N 30/88* | (2023.01) | |
| *H10N 30/00* | (2023.01) | |

(52) U.S. Cl.
CPC ......... *H10N 30/857* (2023.02); *H10N 30/871* (2023.02); *H10N 30/877* (2023.02); *H10N 30/88* (2023.02); *A61B 5/024* (2013.01); *A61B 5/0816* (2013.01); *A61B 2562/029* (2013.01); *A61B 2562/04* (2013.01); *A61B 2562/12* (2013.01); *A61B 2562/164* (2013.01); *H10N 30/708* (2024.05)

(56) References Cited

U.S. PATENT DOCUMENTS

| | | |
|---|---|---|
| 4,148,304 A | 4/1979 | Mull |
| 4,151,831 A | 5/1979 | Lester |
| 4,267,611 A | 5/1981 | Agulnick |
| 4,443,851 A | 4/1984 | Lin |
| 4,465,077 A | 8/1984 | Schneider |
| 4,515,167 A | 5/1985 | Hochman |
| 4,557,273 A | 12/1985 | Stoller |
| 4,827,763 A | 5/1989 | Bourland et al. |
| 4,865,044 A | 9/1989 | Wallace |
| 5,209,238 A | 5/1993 | Sundhar |
| 5,216,599 A | 6/1993 | Uebe |
| 5,385,036 A | 1/1995 | Spillane et al. |
| 5,389,848 A | 2/1995 | Trzaskos |
| 5,619,764 A | 4/1997 | Lopau |
| 5,638,565 A | 6/1997 | Pekar |
| 5,647,078 A | 7/1997 | Pekar |
| 5,651,151 A | 7/1997 | Schild |
| 5,657,762 A | 8/1997 | Coley |
| 6,415,467 B1 | 7/2002 | Bretvin |
| 6,564,410 B2 | 5/2003 | Graebe et al. |
| 6,679,315 B2 | 1/2004 | Cosley |
| 6,715,174 B2 | 4/2004 | Tsai |
| 6,827,128 B2 | 12/2004 | Philpott et al. |
| 7,007,330 B2 | 3/2006 | Kuiper et al. |
| 7,152,412 B2 | 12/2006 | Harvie |
| 7,325,455 B2 | 2/2008 | Campbell et al. |
| 7,395,717 B2 | 7/2008 | DeAngelis et al. |
| 7,492,241 B2 | 2/2009 | Piazza et al. |
| 7,500,536 B2 | 3/2009 | Bulgajewski et al. |
| 7,578,195 B2 | 8/2009 | DeAngelis et al. |
| 7,656,673 B1 | 2/2010 | Fries et al. |
| 7,712,373 B2 | 5/2010 | Nagle et al. |
| 7,948,315 B2 | 5/2011 | Shifrin |
| 8,169,124 B2 | 5/2012 | Lee et al. |
| 8,258,675 B2 | 9/2012 | Ikehara et al. |
| 8,328,420 B2 | 12/2012 | Abreu |
| 8,341,786 B2 | 1/2013 | Oexman |
| 8,353,207 B2 | 1/2013 | Hakansson |
| 8,374,989 B2 | 2/2013 | Lee et al. |
| 8,426,933 B2 | 4/2013 | Yacoubian |
| 8,540,644 B2 | 9/2013 | Husheer |
| 8,598,893 B2 | 12/2013 | Camus |
| 8,768,520 B2 | 7/2014 | Oexman et al. |
| 8,771,204 B2 | 7/2014 | Telfort et al. |
| 8,834,389 B2 | 9/2014 | Schafer |
| 8,961,904 B2 | 2/2015 | Xia |
| 8,979,766 B2 | 3/2015 | Sullivan |
| 8,992,822 B2 | 4/2015 | Rechberg |
| 9,015,885 B2 | 4/2015 | Chapin |
| 9,131,039 B2 | 9/2015 | Behles |
| 9,131,891 B2 | 9/2015 | Shinar et al. |
| 9,216,122 B2 | 12/2015 | Dzioba et al. |
| 9,271,665 B2 | 3/2016 | Sarrafzadeh et al. |
| 9,278,629 B2 | 3/2016 | Stanley et al. |
| 9,354,703 B2 | 5/2016 | Maggiali et al. |
| 9,504,416 B2 | 11/2016 | Young |
| 9,542,028 B2 | 1/2017 | Filiz et al. |
| 9,572,647 B2 | 2/2017 | Couse et al. |
| 9,591,995 B2 | 3/2017 | Blumberg |
| 9,723,719 B2 | 8/2017 | DeRosa et al. |
| 9,733,136 B2 | 8/2017 | Seitz |
| 9,743,913 B2 | 8/2017 | Dillen |
| 9,848,494 B2 | 12/2017 | Huitema et al. |
| 9,848,712 B2 | 12/2017 | Main et al. |
| 9,852,656 B2 | 12/2017 | Ander et al. |
| 9,857,930 B2 | 1/2018 | Sebastian et al. |
| 9,867,597 B1 | 1/2018 | Buard |
| 10,060,802 B1 | 8/2018 | Ragosta |
| 10,123,732 B2 | 11/2018 | Abreu |
| 10,172,593 B2 | 1/2019 | Shinar et al. |
| 10,180,721 B2 | 1/2019 | Hoen et al. |
| 10,194,810 B2 | 2/2019 | Halperin et al. |
| 10,219,749 B2 * | 3/2019 | Kim ...................... A61B 5/113 |
| 10,258,535 B2 | 4/2019 | Lem et al. |
| 10,278,638 B2 | 5/2019 | Dusanter et al. |
| 10,305,017 B2 | 5/2019 | Kondo |
| 10,338,755 B2 | 7/2019 | Podhajny et al. |
| 10,349,895 B2 | 7/2019 | Telfort et al. |
| 10,383,523 B2 | 8/2019 | Yao |
| 10,418,933 B2 | 9/2019 | France et al. |
| 10,463,340 B2 | 11/2019 | Telfort et al. |
| 10,575,829 B2 | 3/2020 | Shinar et al. |
| 10,649,588 B2 | 5/2020 | Amin et al. |
| 10,653,332 B2 | 5/2020 | McGrane et al. |
| 10,763,421 B2 | 9/2020 | Benedict et al. |
| 10,768,066 B2 | 9/2020 | Kamiya et al. |
| 10,779,802 B2 | 9/2020 | Tholen et al. |
| 10,888,268 B2 | 1/2021 | Baltay et al. |
| 10,925,573 B2 | 2/2021 | Martin et al. |
| 10,973,495 B2 | 4/2021 | Vardi et al. |
| 11,020,298 B2 | 6/2021 | Brykalski |
| 11,105,025 B2 | 8/2021 | Boylu et al. |
| 11,191,486 B2 | 12/2021 | Griffin et al. |
| 11,209,957 B2 | 12/2021 | Dryer |
| 11,219,397 B2 | 1/2022 | Wang et al. |
| 11,224,344 B2 | 1/2022 | Ellis et al. |
| 11,253,079 B1 | 2/2022 | Kahn |
| 11,255,736 B2 | 2/2022 | Li |
| 11,259,742 B2 | 3/2022 | Etleb et al. |
| 11,311,111 B2 | 4/2022 | Grutta et al. |
| 11,328,152 B2 | 5/2022 | Chen et al. |
| 11,417,824 B2 | 8/2022 | Li et al. |
| 11,439,370 B2 | 9/2022 | Bongiorno et al. |
| 11,462,673 B2 | 10/2022 | Yoshida et al. |
| 11,517,292 B2 | 12/2022 | Stein et al. |
| 11,540,416 B2 | 12/2022 | Mou et al. |
| 11,642,077 B2 | 5/2023 | Correa Ramirez et al. |
| 11,679,047 B2 | 6/2023 | Wijesundara |
| 11,860,048 B2 | 1/2024 | Bao et al. |
| 2004/0081024 A1 | 4/2004 | Weng |
| 2005/0010128 A1 | 1/2005 | Shiraishi et al. |
| 2005/0257822 A1 | 11/2005 | Smith et al. |
| 2008/0071190 A1 | 3/2008 | Gorodeski et al. |
| 2009/0093687 A1 | 4/2009 | Telfort et al. |
| 2010/0036279 A1 | 2/2010 | Rieth |
| 2011/0107521 A1 | 5/2011 | Alder et al. |
| 2011/0296621 A1 | 12/2011 | McKenna |
| 2012/0242492 A1 | 9/2012 | Grunfeld |
| 2012/0265032 A1 | 10/2012 | Ben-David et al. |
| 2012/0313420 A1 | 12/2012 | Beyerlein et al. |
| 2014/0090489 A1* | 4/2014 | Taylor ...................... G01L 1/00 73/862.626 |
| 2015/0133744 A1 | 5/2015 | Kobayashi et al. |
| 2015/0137994 A1 | 5/2015 | Rahman et al. |
| 2015/0164409 A1 | 6/2015 | Benson et al. |

(56) References Cited

U.S. PATENT DOCUMENTS

| | | | |
|---|---|---|---|
| 2015/0331524 A1* | 11/2015 | McMillen | A61B 5/6843 345/174 |
| 2016/0317370 A1 | 11/2016 | Evans et al. | |
| 2016/0370210 A1 | 12/2016 | Kapusta et al. | |
| 2017/0000347 A1 | 1/2017 | Meftah et al. | |
| 2017/0056644 A1 | 3/2017 | Chahine et al. | |
| 2017/0089775 A1* | 3/2017 | Hsu | G01L 1/16 |
| 2018/0035982 A1 | 2/2018 | Tholen et al. | |
| 2018/0254403 A1 | 9/2018 | Jeong et al. | |
| 2019/0109904 A1 | 4/2019 | Binder et al. | |
| 2019/0110692 A1 | 4/2019 | Pardey et al. | |
| 2019/0117165 A1 | 4/2019 | Zeng et al. | |
| 2019/0167236 A1 | 6/2019 | Maas et al. | |
| 2019/0167237 A1 | 6/2019 | Stein et al. | |
| 2019/0187794 A1 | 6/2019 | Khoshkava | |
| 2019/0223736 A1* | 7/2019 | Wang | H10N 30/883 |
| 2019/0368087 A1 | 12/2019 | Boylu et al. | |
| 2020/0000441 A1 | 1/2020 | Lafon et al. | |
| 2020/0113344 A1 | 4/2020 | Youngblood et al. | |
| 2020/0178887 A1 | 6/2020 | Ramirez et al. | |
| 2020/0405998 A1 | 12/2020 | Franceschetti et al. | |
| 2021/0041287 A1 | 2/2021 | Rimminen et al. | |
| 2021/0085091 A1 | 3/2021 | Brandt et al. | |
| 2021/0295661 A1 | 9/2021 | Tadele et al. | |
| 2021/0356345 A1* | 11/2021 | Li | G02F 1/153 |
| 2022/0047250 A1 | 2/2022 | Clements et al. | |
| 2022/0061699 A1 | 3/2022 | LaBove et al. | |
| 2022/0218314 A1 | 7/2022 | Alexander et al. | |
| 2022/0409095 A1 | 12/2022 | Chuo et al. | |

FOREIGN PATENT DOCUMENTS

| | | |
|---|---|---|
| CN | 106618521 | 5/2017 |
| CN | 107111411 | 8/2017 |
| CN | 109642833 | 4/2019 |
| CN | 111051834 | 4/2020 |
| CN | 111061944 | 4/2020 |
| CN | 213182667 | 5/2021 |
| JP | H08131408 | 5/1996 |
| JP | 2003164527 | 6/2003 |
| JP | 2006230790 | 9/2006 |
| JP | 2008264352 | 11/2008 |
| JP | 2010502338 | 1/2010 |
| JP | 2014212977 | 11/2014 |
| JP | 2019051069 | 4/2019 |
| KR | 20140005289 | 1/2014 |
| KR | 101841365 | 3/2018 |
| KR | 20180079957 | 7/2018 |
| KR | 102087286 | 4/2020 |
| WO | 05/031300 | 4/2005 |
| WO | WO 14/067777 | 5/2014 |
| WO | WO 16/019087 | 2/2016 |
| WO | WO 17/190085 | 11/2017 |
| WO | WO 18/023135 | 2/2018 |
| WO | WO 19/073104 | 4/2019 |
| WO | WO 20/073091 | 4/2020 |
| WO | WO 21/087326 | 5/2021 |

OTHER PUBLICATIONS

U.S. Appl. No. 17/355,442, filed Jun. 23, 2021, Chuo et al.
Robertson et al., "A Compact Modular Soft Surface with Reconfigurable Shape and Stiffness," IEEE/ASME Transactions on Mechatronics, vol. 24, No. 1, Feb. 2019, pp. 16-24.
U.S. Appl. No. 18/687,201, filed Feb. 27, 2024, Tadele et al.
Dorfmeister et al., "A Novel Bi-Stable MEMS Membrane Concept Based on a Piezoelectric Thin Film Actuator for Integrated Switching," vol. 2, No. 912; doi:10.3390/proceedings2130912, Proceedings 2018.
Phelps, Isaac James, "Mechanical characterization of MEMS bi-stable buckled diaphragms," University of Louisville, Electronic Theses and Dissertations, Paper 1129, 2013.
Yi-Yuan Chiu, Wan-Ying Lin, Hsin-Yao Wang, Song-Bin Huang, Min-Hsien Wu; "Development of a piezoelectric polyvinylidene fluoride (PVDF) polymer-based sensor patch for simultaneous heartbeat and respiration monitoring;" Sensors and Actuators A: Physical, vol. 189, 2013, pp. 328-334. (Year: 2013).
M. Komeili, A. Ahrabi, and C. Menon, "Resonance vibration of an optical fiber micro-cantilever using electro-thermal actuation," Mathematical Models in Engineering, vol. 3, No. 1, pp. 1-16, Jun. 2017, (Year: 2017).
Janusas G, Ponelyte S, Brunius A, Guobiene A, Prosycevas I, Vilkauskas A, Palevicius A. Periodical Microstructures Based on Novel Piezoelectric Material for Biomedical Applications. Sensors (Basel). Dec. 15, 2015;15(12):31699-708. (Year: 2015).
Tiffany C. Kaspar et al.; "Tuning piezoelectric properties through epitaxy of La2Ti2O7 and related thin films;" Scientific Reports( 2018) 8:3037 (Year: 2018).
K. R. Rash mi, Arjun Sunil Rao, A. Jayarama, Richard Pinto; "Piezoelectric P(VDF-TrFE) micro cantilevers and beams for low frequency vibration sensors and energy harvesters;" Sensors and Actuators A: Physical, vol. 295, 2019, pp. 574-585. (Year: 2019).
Wikipedia, "Cantilever," https://en.wikipedia.org/wiki/Cantilever; Accessed Apr. 18, 2024 (Year: 2024).

\* cited by examiner

LAYERED SENSOR HAVING MULTIPLE LATERALLY ADJACENT SUBSTRATES IN A SINGLE LAYER

CROSS-REFERENCE TO RELATED APPLICATIONS

This application is a nonprovisional of and claims the benefit under 35 U.S.C. 119(e) of U.S. Provisional Patent Application No. 62/885,028, filed Aug. 9, 2019, and U.S. Provisional Patent Application No. 62/891,195, filed Aug. 23, 2019, the contents of which are incorporated herein by reference as if fully disclosed herein.

FIELD

The described embodiments relate generally to a sleep monitor or other type of sleep sensor. More particularly, the described embodiments relate to a flexible sleep monitor having multiple laterally adjacent substrates in a single layer.

BACKGROUND

Devices used for detecting sleep data may be placed beneath users to collect data as the users sleep. In general, it may be beneficial to make devices for detecting sleep data as thin and/or as flexible as possible to be imperceptible or nearly imperceptible to users. Some devices used for detecting sleep data may include multiple types of sensing mechanisms in a single device. Some devices are assembled by stacking multiple layers on top of one another, each layer including the same material(s) and/or a single type of sensing mechanism along the entire layer. This may require at least one layer for each type of sensing mechanism, and may cause traditional devices to be rigid and thick, resulting in discomfort for users and reducing users' willingness to continue using the devices.

SUMMARY

Embodiments of the systems, devices, methods, and apparatuses described in the present disclosure are directed to a flexible sleep monitor having multiple substrates in a single layer and methods for manufacturing or assembling a layered sensor having multiple substrates positioned laterally adjacent to one another in a single layer.

The embodiments described herein may include a layered sensor for a flexible sleep monitor. The layered sensor may include a first flexible layer, a second flexible layer that is substantially parallel to the first flexible layer, a substrate layer, a first electrode, and a second electrode. The substrate layer may be positioned between the first flexible layer and the second flexible layer and may include a first substrate and a second substrate. The first substrate may be formed of a first material and may be configured to generate electric charge in response to a force applied to the flexible sleep monitor. The second substrate may be formed of a second material different than the first material and may be positioned laterally adjacent to the first substrate. The first electrode may be disposed on a first surface of the first substrate. The second electrode may be disposed on a second surface of the second substrate. The substrate layer may be flexible. The first electrode and the second electrode may be configured to be electrically coupled to a processing unit configured to determine a sleep characteristic using a signal received from at least one of the first electrode or the second electrode.

The embodiments described herein may further include a flexible sleep monitor that includes an enclosure and a layered sensor. The layered sensor may be at least partially surrounded by the enclosure. The layered sensor may include a substrate layer and a flexible layer. The substrate layer may be positioned within the enclosure and may include a first substrate formed from a first material and a second substrate positioned laterally adjacent to the first substrate and formed from a second material. The flexible layer may be positioned between the substrate layer and a portion of the enclosure and may comprise a third substrate. The substrate layer may be formed by interdigitating first members of a first sheet section of a first sheet comprising the first substrate with second members of a second sheet section of a second sheet comprising the second substrate to form a combined sheet.

The embodiments described herein may further include a method for forming a layered sensor for a sleep monitor that includes the step of cutting a first flexible sheet comprising a piezoelectric material into a first portion comprising a first head and a first set of fingers extending from the first head and a second portion comprising a second head and a second set of fingers extending from the second head and interdigitated with the first set of fingers. The method may further include separating the first portion of the first flexible sheet from the second portion of the first flexible sheet and interdigitating the first set of fingers with a third set of fingers of a second flexible sheet to form a combined sheet. The method may further include attaching the combined sheet to one or more additional sheets to form a stack, removing the first head from the stack, and separating the stack into two or more sensors.

The embodiments described herein may also include a layered sensor. The layered sensor may include a first flexible layer; a second flexible layer that is substantially parallel to the first flexible layer; and a substrate layer positioned between the first flexible layer and the second flexible layer. The substrate layer may include a first substrate formed of a first material, and configured to generate electric charge in response to a force applied to the layered sensor, and a second substrate formed of a second material different from the first material and positioned laterally adjacent to the first substrate. The layered sensor may further include a first electrode disposed on a first surface of the first substrate, and a second electrode disposed on a second surface of the first substrate, the second surface opposite the first surface. The substrate layer may be flexible, and at least a portion of the first substrate may have a curved shape extending parallel to the substrate layer. In some cases, the curved shape may be a serpentine shape.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1A:
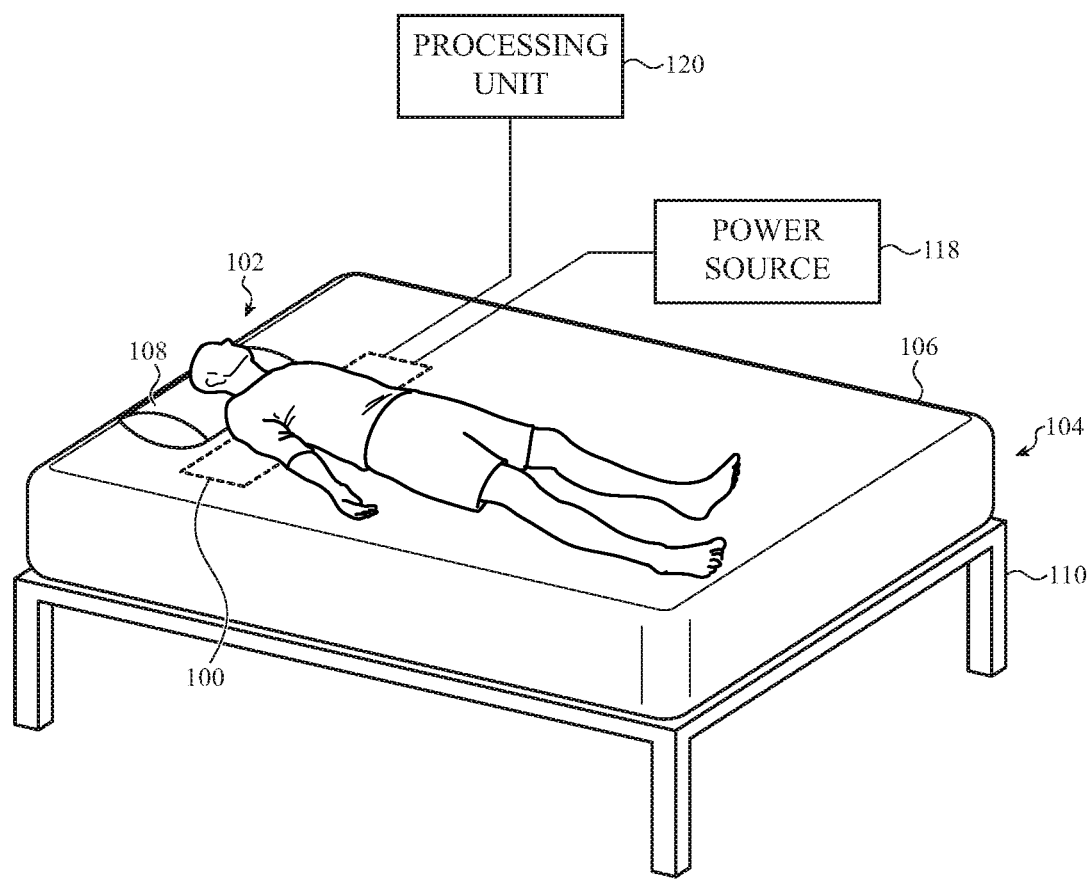
FIG. 1A shows an example environment for using a sleep monitor.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to layered sensors having multiple substrates in a single layer, such as a sleep monitor or other sensor(s) for use in determining one or more sleep characteristics of a user's sleep. The sleep monitor may be sufficiently thin and/or flexible so that the sleep monitor, when positioned in a bed beneath the user, does not cause discomfort. In some cases, the sleep monitor includes a layered sensor with at least one layer that is formed by interdigitating fingers of a first sheet with fingers of a second sheet. The interdigitated fingers may allow multiple substrates, materials, and/or sensing mechanisms to be combined together in a single layer. In particular, multiple different substrates may be included in a single layer and positioned laterally adjacent to one another. This may provide numerous advantages over traditional sleep monitors, including reducing wasted material (and decreasing material costs), reducing an overall thickness of the sleep monitor, increasing a flexibility of the sleep monitor, and simplifying manufacturing. In some cases, the sleep monitor includes a layered sensor having a serpentine-shaped sensing substrate disposed between non-sensing substrates (or between different portions of a non-sensing substrate).

As used herein, a "substrate" may be used to refer to a block or mass of common material. As used herein, a "layer" may be used to refer to one or more laterally adjacent components (e.g., substrates) generally extending between a first side of a layered sensor and a second, opposite side of the layered sensor. The layers described herein are typically, but not necessarily, parallel to the top surface and/or bottom surface of the flexible sleep monitor and/or the layered sensor, and are typically, but do not necessarily, extend from a portion of the enclosure defining a first side of the flexible sleep monitor to a portion of the enclosure defining a second side of the flexible sleep monitor. As used herein, components are "laterally adjacent" when those components are positioned next to one another on the same layer. Laterally adjacent components may abut or otherwise touch one another or may be separated by a gap. If separated by a gap, that gap is typically less than the thickness of the component(s).

As noted above, the sleep monitor may be placed beneath a user as the user is in bed and may detect input signals related to movement, biometrics, sounds (e.g., cardiac and/or respiratory sounds), ambient characteristics, and the like while the user is in bed. The sleep monitor may provide output signals corresponding to the input signals to a processing unit. The processing unit may determine one or more sleep characteristics of the user using the output signals provided by the sensor of the sleep monitor. As used herein, "sleep characteristics" may refer to data or analysis regarding a user's sleep, including sleep duration, in-bed duration, bedtime (e.g., time of day the user gets in bed), sleep time (e.g., time of day the user falls asleep), duration to fall asleep, duration awake in bed, duration away from bed, wake-up time (e.g., time of day the user wakes up), sleep efficiency (e.g., sleep duration divided by in-bed duration), heart information (e.g., instantaneous heart rate, average heart rate, maximum heart rate, minimum heart rate), breathing information (e.g., instantaneous breathing rate, average breathing rate, maximum breathing rate, minimum breathing rate), snoring information (e.g., snoring duration, snoring start time(s), snoring end time(s)), and ambient characteristics (e.g., temperature, humidity level).

As noted above, the layered sensor of the sleep monitor may include multiple sensing mechanisms, and in some cases, substrates that form at least portions of multiple sensing mechanisms are included in a single layer of the layered sensor, and may be positioned laterally adjacent to one another. In some cases, the layered sensor includes one or more contact sensing mechanisms (e.g., touch and/or proximity sensing mechanisms) for detecting input signals for use in determining sleep characteristics. The contact sensing mechanism may be capable of detecting whether a user is in bed, for example, by detecting that the user is contacting the bed and/or the sleep monitor. The contact sensing mechanism may additionally be capable of detecting a positioning of the user in bed, (e.g., whether the user is sleeping on his or her back, side, or stomach, a relative positioning of the user in the bed, or the like). The contact sensing mechanisms may include a substrate and capacitive sensing mechanisms that include one or more electrodes (e.g., electrodes positioned on a surface of or embedded within a substrate) for determining whether a user is in contact with and/or proximate to the sleep monitor. The contact sensing mechanisms may use mutual-capacitive sensing techniques and/or self-capacitive sensing techniques and, in some cases, electrodes coupled to opposite sides of the sensing substrate may be coupled to a differential sensor (e.g., a differential sense amplifier).

In some cases, the sleep monitor includes one or more force sensing mechanisms for detecting input signals for use in determining sleep characteristics. The force sensing mechanisms may be capable of detecting whether a user is in bed, a positioning of the user in bed, heart information, breathing information, and the like. The force sensing mechanisms may include piezoelectric force sensing mechanisms that include a piezoelectric substrate configured to generate electric charge in response to a force applied to the sleep monitor and one or more electrodes electrically coupling the piezoelectric substrate to sensing circuitry of the sleep monitor. The generated charge may change an output signal of the piezoelectric substrate that is transmitted to the sensing circuitry. The sensing circuitry may be electrically coupled to a processing unit configured to determine sleep characteristics from the output signal. In some cases, the piezoelectric substrate is formed from a flexible piezoelectric material so that the sleep monitor may be flexible. Examples of flexible piezoelectric materials include polyvinylidene fluoride (PVDF), polyvinylidenefluoride-co-trifluoroethylene (PVDF-TrFE), and other ferroelectric polymers. In some cases, the piezoelectric substrate may be cut or patterned into a serpentine, curved, or arcuate shape, which may make the piezoelectric material even more flexible and/or help the piezoelectric substrate better match the acoustic impedance of human skin. A serpentine, curved, or arcuate shape can help to reduce the strain experienced by a material.

As noted above, in some cases, one or more substrates of one or more force sensing mechanisms and one or more substrates of one or more contact sensing mechanisms may be positioned in the same substrate layer of the layered sensor. For example, a piezoelectric substrate for a force sensing mechanism and a substrate for a contact sensing mechanism may be included in a single substrate layer. The piezoelectric substrate may be positioned laterally adjacent to the substrate for the contact sensing mechanism. The substrate layer that includes the multiple laterally adjacent substrates may be formed by interdigitating fingers of a first sheet with fingers of a second sheet. In some cases, the fingers of the first sheet include one or more substrates for force sensing mechanisms and the fingers of the second sheet include one or more substrates for contact sensing mechanisms. In some cases, once the sheets are interdigitated, they are separated into multiple different layered sensors. Each of the multiple different layered sensors may include a finger of the first sheet (including one or more force sensing mechanisms) and a finger of the second sheet (including one or more contact sensing mechanisms).

As noted above, the combined elements of the substrate layer may allow multiple materials and/or substrates to be placed in a single layer. This may provide numerous advantages over traditional sleep monitors, including reducing wasted material (and decreasing material costs), reducing an overall thickness of the sleep monitor, increasing a flexibility of the sleep monitor, and simplifying manufacturing. The materials used to form certain substrates (e.g., PVDF for piezoelectric substrates for force sensing) may be expensive compared to materials used to form other substrates (e.g., materials used for substrates for contact sensing). The properties provided by the more expensive materials may not be required at all locations across a layered sensor. For example, contact sensing mechanisms may not require a piezoelectric substrate, and may instead include substrates formed from less expensive materials in the same layer as a piezoelectric substrate for force sensing. Layered sensors having a piezoelectric substrate and one or more other substrates formed from different materials on a single layer may require less PVDF compared to layered sensors having an entire layer of PVDF, thereby resulting in reduced material costs.

The sensors discussed herein may include a single layer or multiple layers. The sensors may include one or more substrate layers, flexible layers, support layers, adhesive layers, or the like. The support layers and/or adhesive layers may provide advantages, including simplifying the manufacturing process by making separating and/or interdigitating the sheet sections easier. The support layers may provide rigidity and other structural support to the fingers of the sheet sections so that they may maintain their shape during manufacturing, for example, so that they may be interdigitated with one or more additional sheet sections. Preferably, all of the layers stacked with the piezoelectric layer, and any components, such as electrodes or shields, are compliant and have a modulus of elasticity that is similar to or lower than (and preferably significantly lower than) the modulus of elasticity of the piezoelectric layer, so that there is a low shear strain between layers, and so that the other components and layers do not interfere with stretch or contraction of the piezoelectric layer and do not significantly alter the sensing capability of the piezoelectric layer.

In some cases, the adhesive layer(s) attach a substrate (e.g., a PVDF layer) to one or more support layers. The adhesive layers may include alternating regions corresponding to fingers of the sheet sections (e.g., corresponding to a cutting pattern of the sheet used to form the substrate). The alternating regions may have different adhesive strength from one another to facilitate separating the sheet sections of a sheet during manufacturing. The layered sensor may include additional layers, including ground layers. In some cases, one or more ground layers provide reference voltage(s) for the one or more contact sensing mechanisms, the one or more force sensing mechanisms, or other sensing mechanisms or components of the layered sensor.

The term "attached," as used herein, may be used to refer to two or more elements, structures, objects, components, parts or the like that are physically affixed, fastened, and/or retained to one another. The term "coupled," as used herein, may be used to refer to two or more elements, structures, objects, components, parts or the like that are physically attached to one another, operate with one another, communicate with one another, are in electrical connection with one another, and/or otherwise interact with one another. Accordingly, while elements attached to one another are coupled to one another, the reverse is not required. As used herein, "operably coupled" may be used to refer to two or more devices that are coupled in any suitable manner for operation and/or communication, including wiredly, wirelessly, or some combination thereof.

These and other embodiments are discussed with reference to FIGS. 1A-8. However, those skilled in the art will readily appreciate that the detailed description given herein with respect to these figures is for explanatory purposes only and should not be construed as limiting.

FIG. 1A shows an example environment for using a sleep monitor 100 (shown in phantom). As shown in FIG. 1A, the sleep monitor 100 may be positioned beneath a user 102 as the user is in a bed 104. The sleep monitor 100 may include one or more sensing mechanisms that detect input signals related to movement, biometrics (e.g., heart rate, breathing rate, etc.), sounds (e.g., cardiac and/or respiratory sounds), ambient characteristics, and the like while the user is in bed. For example, in some cases, the sleep monitor 100 detects input signals relating to proximity (or contact) and force(s) at particular locations over time.

The sleep monitor 100 or one or more components thereof (e.g., a layered sensor) may provide output signals corresponding to the detected input signals to a processing unit 120 that is operably coupled to the sleep monitor 100. The processing unit 120 may determine one or more sleep characteristics of the user using the output signals provided by the sleep monitor 100. The processing unit 120 may be a component of the sleep monitor 100 or it may be a component of a separate device, such as a smartphone or other computing device. In some cases, the processing unit 120 is a processing unit of an electronic device that includes a display configured to provide a graphical output. The processing unit 120 may change the graphical output of the display in response to determining the one or more sleep characteristics of the user. For example, the electronic device may display graphical objects and/or other information regarding the sleep characteristics.

The sleep monitor 100 may be positioned above or beneath a mattress 106 and/or bed frame 110 of the bed 104. The sleep monitor 100 may be positioned above or beneath bedding of the bed 104, including a mattress protector, sheets, blankets, and the like. In some cases, the sleep monitor 100 is positioned above the mattress 106 and beneath at least some layers of bedding. For example, the sleep monitor 100 may be positioned above a mattress protector, but beneath a bottom sheet of the bedding. In some cases, the sleep monitor 100 includes adhesive along one or more surfaces so that the sleep monitor 100 may be attached or coupled to the mattress 106 or bedding of the bed (e.g., a mattress protector). In some cases, the sleep monitor 100 is placed between approximately 10 and 40 centimeters from a pillow 108. The sleep monitor 100 may be centered in a sleeping area of the user 102.

The sleep monitor 100 may be operably coupled to a power source 118. The power source 118 can be implemented with any device capable of providing energy to the sleep monitor 100. For example, the power source 118 may be one or more batteries or rechargeable batteries. Additionally or alternatively, the power source 118 can be a power connector or power cord that connects the sleep monitor 100 to another power source, such as a wall outlet.

In some cases, at least a portion of the power source 118 may be part of the sleep monitor 100 and may include a sensing mechanism for detecting inputs. For example, in some cases, the power source 118 includes a connector (e.g., a USB cable) that includes a temperature sensing mechanism and/or a humidity sensing mechanism for sensing a temperature and a humidity level of the environment surrounding the sleep monitor 100. In some cases, one or more sensing mechanisms (e.g., temperature and humidity sensing mechanisms) may be located at other positions of the sleep monitor 100 and/or one or more sensing mechanisms may be remote to the sleep monitor 100 and operably connected to the processing unit 120 and/or the sleep monitor 100.

Figure 1B:
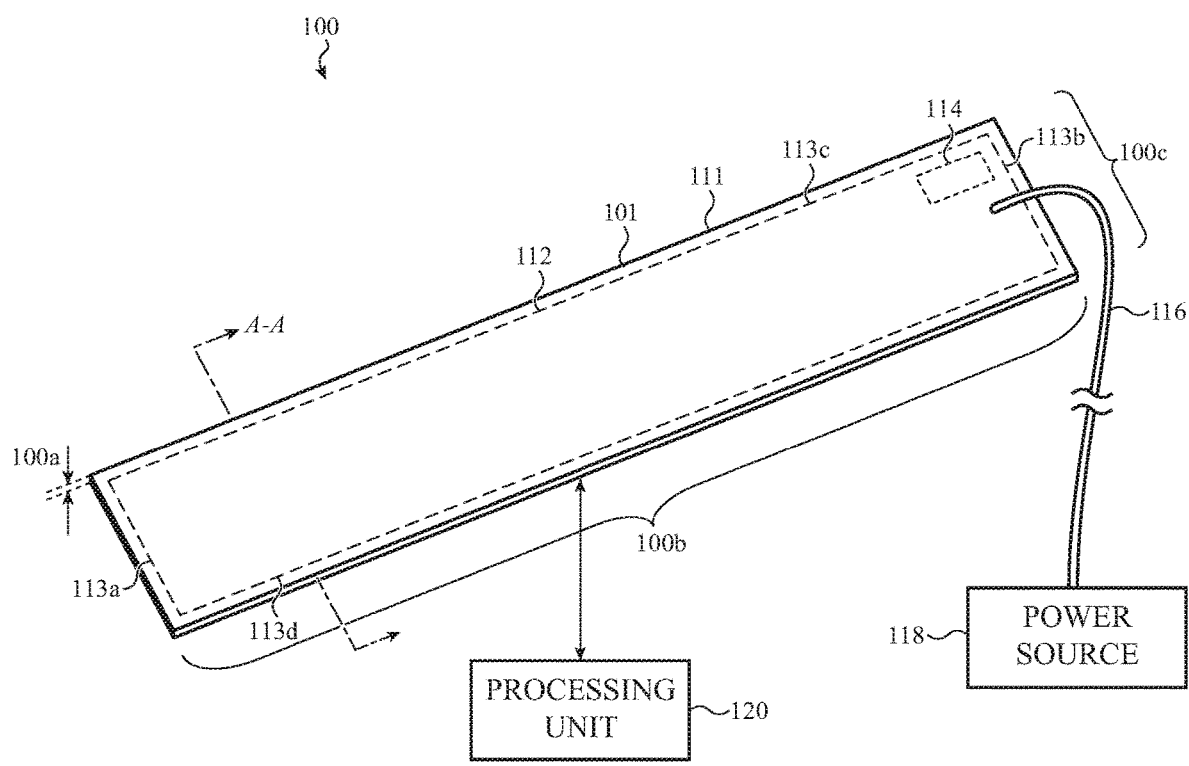
FIG. 1B shows the example sleep monitor of FIG. 1A, including a layered sensor.

As noted above, in some cases, the sleep monitor 100 includes a layered sensor for detecting inputs. FIG. 1B shows the example sleep monitor 100 that may include a layered sensor 112 (shown in phantom). In some cases, the layered sensor 112 may include one or more sensing mechanisms for detecting inputs that may be used to determine sleep characteristics. The layered sensor 112 may include one or more contact sensing mechanisms for detecting contact with or proximity to the sleep monitor 100 and/or locations thereof. The layered sensor 112 may include one or more force sensing mechanisms for detecting force(s) applied to the sleep monitor 100. In some cases, as discussed below, substrates for the contact sensing mechanism(s) and substrates the force sensing mechanism(s) are positioned laterally adjacent to one another and/or in the same layer of the layered sensor 112. For example, the layered sensor 112 may include an interdigitated substrate layer that includes substrates for contact sensing mechanism(s) and substrates for force sensing mechanism(s) on a single layer. This may provide advantages over traditional sensors, including reducing a thickness and increasing a flexibility of the sleep monitor 100 so that the sleep monitor is more comfortable and/or less perceptible during use. For example, the user 102 may be less able to perceive the sleep monitor 100 during use, thereby increasing a comfort of the sleep monitor.

As noted above, as used herein, a "layer" may be used to refer to one or more laterally adjacent components generally extending between a first side of the layered sensor and a second, opposite side of the layered sensor. For example, a layer may extend between a first side 113a of the layered sensor 112 to a second side 113b, opposite the first side 113a, of the layered sensor 112. Similarly, a layer may extend between a first side 113c of the layered sensor 112 to a second side 113d, opposite the first side 113c, of the layered sensor 112. The layers described herein are typically, but not necessarily, parallel to the top surface 101 and/or bottom surface (not shown in FIG. 1B) of the flexible sleep monitor 100 and/or the layered sensor 112, and are typically, but do not necessarily, extend from a portion of the enclosure 111 defining a first side of the flexible sleep monitor 100 to a portion of the enclosure defining a second side of the flexible sleep monitor.

The force sensing mechanisms may be piezoelectric force sensing mechanisms that include a piezoelectric substrate configured to generate electric charge in response to a force applied to the sleep monitor 100 and one or more electrodes electrically coupling the piezoelectric substrate to sensing circuitry 114 of the sleep monitor. The generated charge may change an output signal of the piezoelectric substrate that is transmitted to the sensing circuitry. The sensing circuitry may be electrically coupled to a processing unit configured to determine sleep characteristics from the output signal.

In some cases, the piezoelectric substrate is formed from a flexible piezoelectric material that allows the sleep monitor to be flexible. Examples of flexible piezoelectric materials include PVDF, PVDF-TrFE, and other ferroelectric polymers.

The sleep monitor 100 may include sensing circuitry 114 (shown in phantom as it is inside the sleep monitor, and thus not visible in FIG. 1B). The sensing circuitry 114 may include one or more circuits or processors operably connected to and configured to receive input signals from the sensing mechanisms of the layered sensor 112 and/or other sensors or sensing mechanisms of the sleep monitor 100. The sensing circuitry may be configured to provide output signals corresponding to the received input signals to the processing unit 120 (or to a communication interface of a device that includes the processing unit 120). In some cases, the sensing circuitry 114 includes at least a portion of a communication interface that operably couples the sleep monitor 100 to the processing unit 120. In some cases, the communication interface includes a wired connection (e.g., a connector or cable) to operably couple the sleep monitor 100 to the processing unit 120. In some cases, the communication interface includes a wireless connection (e.g., WiFi, BLUETOOTH LE, or the like) to operably couple the sleep monitor 100 to the processing unit 120.

In some cases, the sleep monitor 100 includes a microphone for detecting audio inputs. In some cases, the audio inputs may be used to detect snoring or other audio data as the sleep monitor 100 is used. In some cases, the microphone is a microphone of a separate device, such as a device containing the processing unit 120.

The sleep monitor 100 may include an enclosure 111 or other external layer that at least partially surrounds the layered sensor 112 and/or other components of the sleep monitor 100. The enclosure 111 may contain and/or protect the layered sensor 112 and/or other components of the sleep monitor 100. In some cases, the enclosure 111 is flexible. One or more surfaces of the enclosure 111 may include an adhesive or a high-friction material configured to maintain the sleep monitor 100 in place. As noted above, in various embodiments, the sleep monitor 100 may include multiple layered sensors and/or other sensors.

In some cases, a thickness 100a of the sleep monitor 100 is much smaller than its length 100b and/or width 100c. For example, the thickness 100a of the sleep monitor 100 may be less than approximately ten percent, five percent, or even one percent of the width 100c of the sleep monitor. The thickness 100a of the sleep monitor 100 may be less than approximately one percent, one half of one percent, or even one tenth of one percent of the length 100b of the sleep monitor. In some cases, a thickness of the layered sensor 112 is much smaller than its length and/or width. For example, the thickness of the layered sensor 112 may be less than approximately ten percent, five percent, or even one percent of the width of the layered sensor. The thickness of the layered sensor 112 may be less than approximately one percent, one half of one percent, or even one tenth of one percent of the length 100b of the layered sensor. The dimensions of the sleep monitor 100 and/or the layered sensor 112 may provide numerous advantages, including increasing a flexibility of the sleep monitor 100, improving comfort of the sleep monitor, and/or reducing a user-perceptibility of the sleep monitor during use.

The thickness 100a of the sleep monitor 100 may be reduced compared to traditional sleep monitors by including components (e.g., substrates) of multiple sensing mechanisms in a single layer of the layered sensor 112. As noted above, in some cases, one or more substrates of force sensing mechanisms and one or more substrates of contact sensing mechanisms may be positioned in the same substrate layer of the layered sensor 112. The substrate layer may include a combined sheet formed by interdigitating fingers of a first sheet with fingers of a second sheet. In some cases, the fingers of the first sheet include one or more force sensing mechanisms and the fingers of the second sheet include one or more contact sensing mechanisms.

As noted above, the interdigitated combined sheets of the substrate layer may allow multiple substrates to be combined together in a single layer. This may provide numerous advantages over traditional sleep monitors, including reducing wasted material (and decreasing material costs), reducing an overall thickness of the sleep monitor, increasing a flexibility of the sleep monitor, and simplifying manufacturing. The materials used to form certain substrates (e.g., PVDF for piezoelectric substrates for force sensing) may be expensive compared to materials used to form other substrates (e.g., materials used for substrates for contact sensing). The properties provided by the more expensive materials may not be required at all locations across a layered sensor. For example, contact sensing mechanisms may not require a piezoelectric substrate, and may instead include substrates formed from less expensive materials in the same layer as a piezoelectric substrate for force sensing. Layered sensors having a piezoelectric substrate and one or more other substrates formed from different materials on a single layer may require less PVDF compared to layered sensors having an entire layer of PVDF, thereby resulting in reduced material costs.

Figure 2:
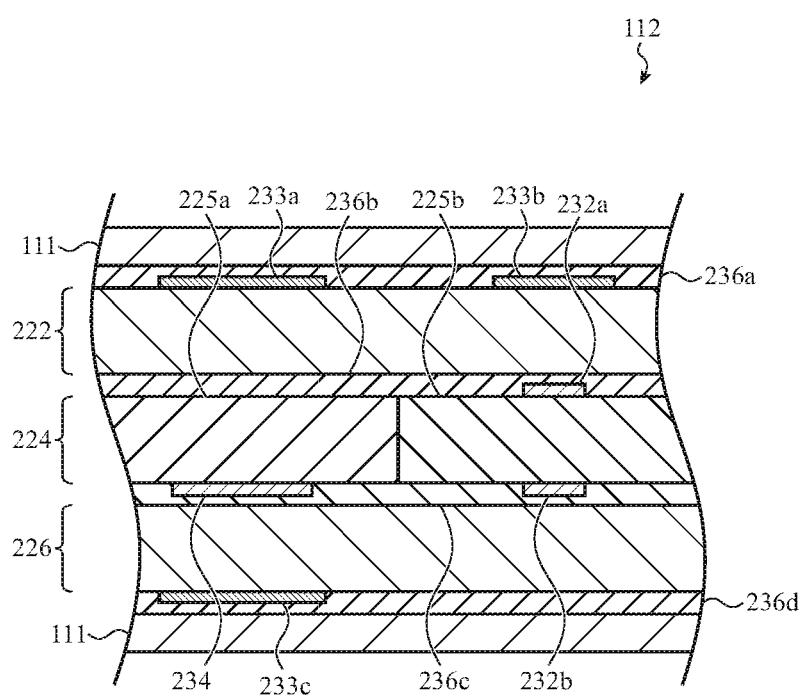
FIG. 2 shows a cross-section view of the example layered sensor of FIG. 1B, taken through section line A-A of FIG. 1B.

FIG. 2 shows a cross-section view of the example sleep monitor 100, including the layered sensor 112, taken through section line A-A of FIG. 1B. As shown in FIG. 2, the layered sensor 112 of the sleep monitor 100 may include multiple layers positioned within or at least partially surrounded by the enclosure 111 of the sleep monitor. The layered sensor 112 may include layers 222, 224, and 226. In some cases, the layer 224 is a substrate layer that includes multiple substrates 225a, 225b formed from different materials and positioned laterally adjacent to one another. In some cases, the substrate layer 224 is formed by interdigitating two or more sheet sections of sheets formed of different materials during a manufacturing process, as discussed in more detail below with respect to FIGS. 3-4H. For example, the substrate 225a may be a substrate that forms part of or supports a contact sensing mechanism, and the substrate 225b may be a piezoelectric substrate that forms part of a force sensing mechanism. In some cases, the substrate 225a does not include a piezoelectric material. The layers 222, 226 may be any type of layer, including ground layers, adhesive layers, substrate layers, support layers, and the like.

The layers 222, 226 may be ground layers that provide reference voltage(s) for the one or more contact sensing mechanisms or the one or more force sensing mechanisms of the substrate layer 224. For example, one or more of the ground layers 222, 226 may serve as a ground plane for capacitive sensing (e.g., for contact sensing), piezoelectric sensing (e.g., force sensing), or the like. In some cases, the layer 222 and/or the layer 226 include a single substrate across the entire layer. In other cases, the layer 222 and/or the layer 226 include multiple substrates in a single layer (similar to layer 224).

The substrates 225a, 225b may cooperate to define a substantially continuous top surface of the substrate layer 224 facing the layer 222 and/or a substantially continuous bottom surface of the substrate layer facing the layer 226. As used herein, the term "substantially continuous" may refer to a surface that is planar and/or has a smooth curvature, and does not have substantial discontinuities or gaps. The substrate layer 224 may be formed by interdigitating members (e.g., fingers) of two or more sheets of different materials during a manufacturing process. In some cases, the width (e.g., left to right with respect to FIG. 2) of one or more laterally adjacent substrates 225a, 225b are substantially equal (e.g., differing by less than 20%, 10%, or even 1%).

The substrates of the layered sensor 112 (e.g., the substrates of the layers 222, 224, 226) may be formed of any suitable material, including polymers, foams, and the like. In some cases, one or more substrates (e.g., the substrate 225b)

include PVDF, and one or more other substrates (e.g., the substrate 225a) do not include PVDF. As noted above, including multiple substrates in one or more layers of the layered sensor 112 may provide numerous advantages, including reducing the cost of materials. For example, PVDF may be more expensive than materials used for non-piezoelectric sheet sections, and including a substrate without PVDF on the same layer as a substrate with PVDF may reduce the amount of PVDF required for the layered sensor 112, thereby reducing the cost of the materials used to form the flexible sensor. In some cases, the substrate 225a and/or the substrates of the layers 222 and 226 may be or include polyurethane (PU) or thermoplastic polyurethane (TPU) substrates. The PU or TPU substrates may be selected to have relatively less hysteresis and relatively elastic strain when undergoing deformation or strain cycling. In some cases, the substrate 225a and/or the substrates of the layers 222 and 226 may be or include shape memory polymer (SMP) substrates (i.e., PU substrates having properties such as good shape recovery, shape retention, and shock absorption over a wide temperature range of interest). One useful SMP is poly(urethane-oxazolidone) (PUO, also known as oxazolidone-modified PU), which has a relatively linear $E_g/E_r$ ratio over a wide temperature range, where $E_g$ is a glassy state modulus of the PUO, and $E_r$ is a rubber modulus of the PUO. The $E_g/E_r$ ratio and shape recovery of a PUO substrate are generally proportional to the PUO's oxazolidone content.

As shown in FIG. 2, the layered sensor 112 includes one or more electrodes positioned along and/or within the substrates of the layers 222, 224, 226. For example, one or more electrodes may be disposed along a surface of and/or at least partially within the substrates of the substrate layer 224 to carry sensor signals (e.g., input signals or output signals) to sensing circuitry of the sleep monitor 100. For example, as shown in FIG. 2, the substrate 225b may include electrodes 232a, 232b along a top surface and a bottom surface, respectively. The electrodes 232a, 232b may be components of the force sensing mechanism of the layered sensor 112. The substrate 225a may include an electrode 234 disposed along a surface of the substrate 225a (e.g., an electrode that forms at least a portion of a capacitive contact sensing mechanism). The layers 222, 226 may include electrodes 233a, 233b, 233c for providing signals (e.g., power, reference voltage signals, etc.) to and/or transmitting signals from the sensor 112.

The electrodes of the layered sensor 112 may be formed by depositing (e.g., printing, attaching with a conductive adhesive) a metallic film or other material on a surface of the substrate(s). In some cases, the materials of the electrodes may differ for different sheet sections. For example, the electrodes 232a, 232b may include different materials as the electrodes 234. In some cases, the electrodes 232a, 232b include silver for more precise detection of piezoelectric charge generated by the piezoelectric substrate 225b. Other examples of electrode materials include silver (e.g., silver/silver sulfate, silver/silver chloride), copper (copper/copper sulfate, copper nickel), mercury (calomel), aluminum, gold (AgNW), and the like. The electrodes 233a, 233b, 233c, 234 may include different materials from the materials used for the electrodes 232a, 232b, such as copper, that may be less expensive than the materials used in the electrodes 232a, 232b, thereby reducing the cost of the flexible sensor 212.

In some cases, the layered sensor 112 includes one or more adhesive layers 236a, 236b, 236c, 236d between layers of the layered sensor and/or between the layered sensor and other device components, such as the enclosure 111. For example, the layered sensor 112 may include an adhesive layer 236a between the enclosure 111 and the layer 222, an adhesive layer 236b between the layer 222 and the substrate layer 224, an adhesive layer 236c between the substrate layer 224 and the layer 226, and/or an adhesive layer 236d between the layer 226 and the enclosure 111. The adhesive layers 236a, 236b, 236c, 236d may include pressure-sensitive adhesive or another type of adhesive and may attach one or more portions of the sensor and/or the sleep monitor together.

Figure 3:
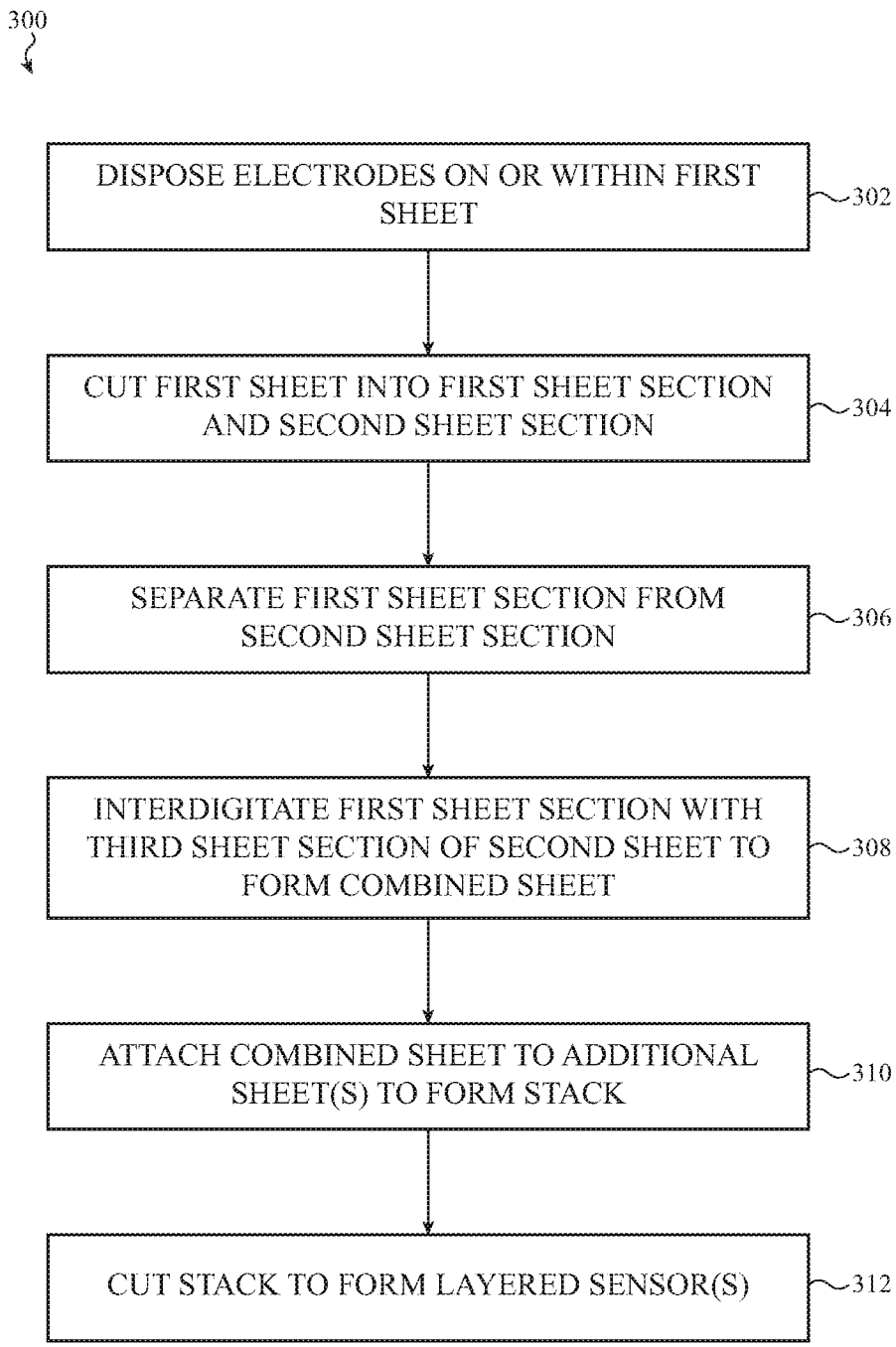
FIG. 3 shows a flowchart of an example method for manufacturing a layered sensor having multiple substrates in a single layer.

FIG. 3 shows a flowchart of an example method 300 for manufacturing a layered sensor having multiple substrates in a single layer. FIGS. 4A-4H show an example layered sensor having a substrate layer with multiple laterally adjacent substrates, similar to the sensor 112 discussed above with respect to FIGS. 1B and 2, being formed using a process similar to the method 300.

Figure 4A:
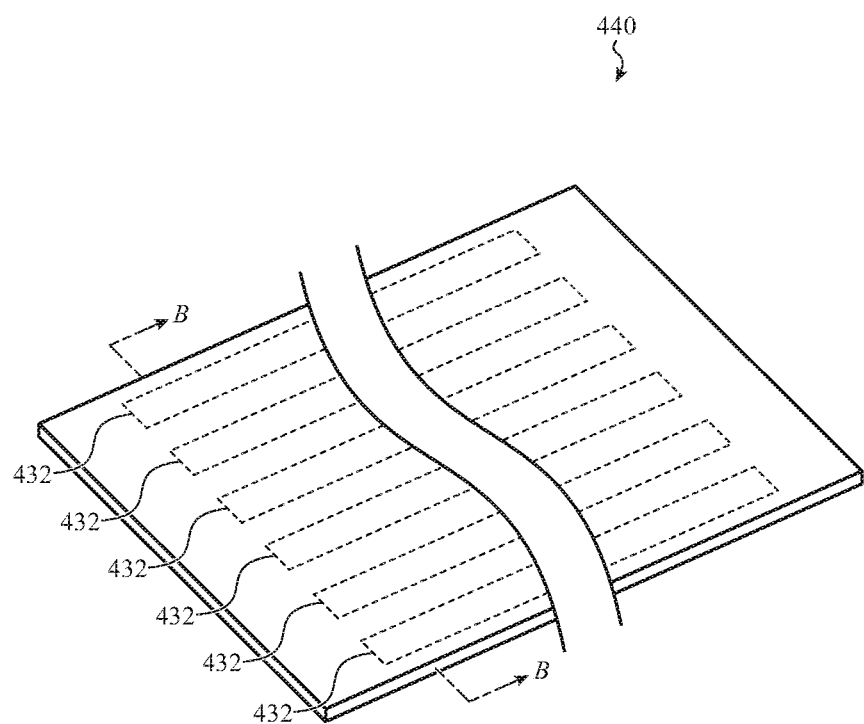
FIGS. 4A-4H show an example sensor having multiple substrates in a single substrate layer being formed.

At block 302 of FIG. 3, one or more electrodes are disposed on or within a first sheet. For example, as shown in FIG. 4A, electrodes 432 (shown in phantom) may be disposed on or within an example sheet 440. The electrodes may be applied directly to the first sheet (e.g., printed) or attached using an adhesive (e.g., a conductive adhesive).

Figure 4B:
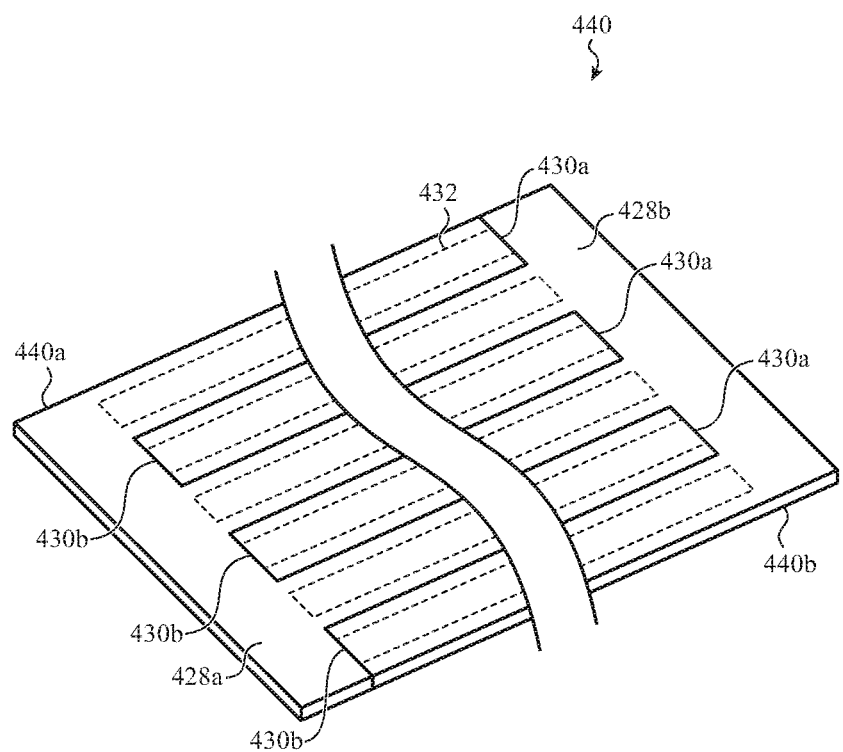

At block 304 of FIG. 3, the first sheet is cut into a first sheet section and a second sheet section. For example, as shown in FIG. 4B, the sheet 440 may be cut into a first sheet section 440a and a second sheet section 440b. The sheet 440 may be cut according to a pattern such that the first sheet section 440a is interdigitated with the second sheet section 440b as shown in FIG. 4B. The cutting pattern may result in the sheet section 440a, 440b having alternating interdigitated members 430a, 430b as shown in FIG. 4B. Each interdigitated member 430a, 430b may extend from a respective head 428a, 428b. Each interdigitated member 430a, 430b may include one or more electrodes 432 extending along a length of the interdigitated members 430a, 430b. Alternating electrodes 432 of the sheet 440 may be located on or within different sheet sections 440a, 440b. Said another way, a first electrode 432 may be positioned on or within the first sheet section 440a, and a second electrode 432 that is adjacent to the first electrode 432 may be positioned on or within the second sheet section 440b. In some cases, the cutting pattern includes segments between each pair of electrodes 432 (e.g., cuts extending along a part of a length of the sheet 440) and segments between alternating electrodes and heads 428a and 428b (e.g., extending along a part of a width of the sheet 440).

Figure 4C:
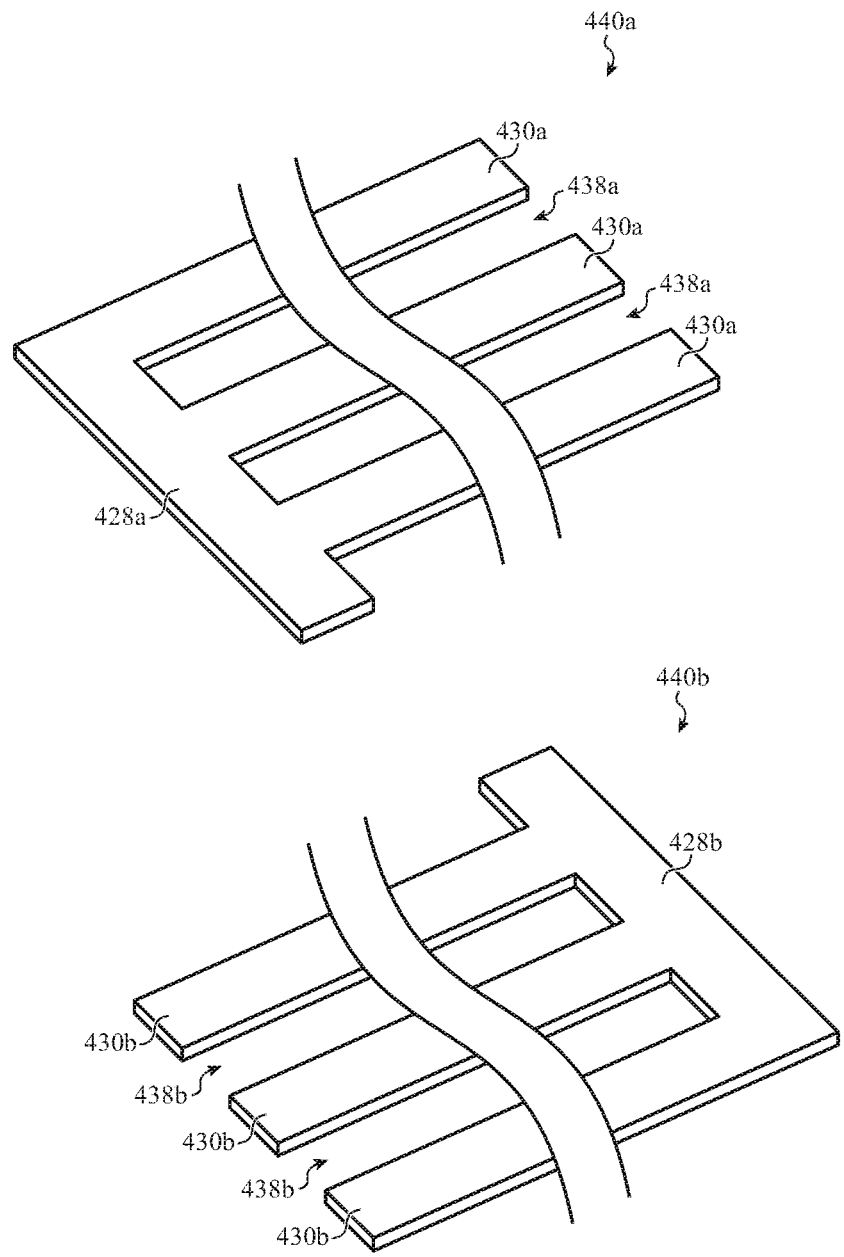
Figure 4D:
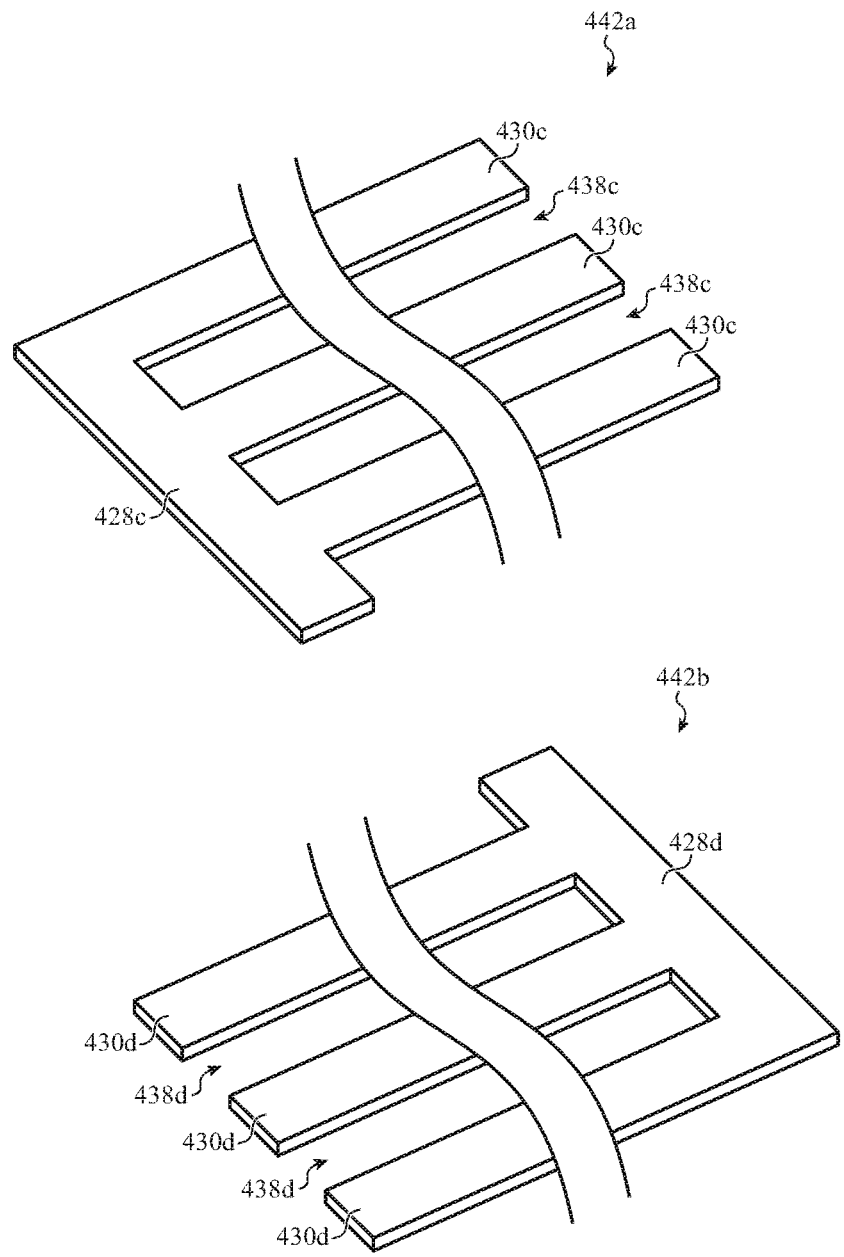

At block 306 of FIG. 3, the first sheet section of the first sheet is separated from the second sheet section of the first sheet. For example, as shown in FIG. 4C, the sheet sections 440a, 440b may be separated from one another. As noted above, each sheet section 440a, 440b may include a head 428a, 428b and members (e.g., fingers) 430a, 430b extending from the head. In some cases, the members 430a, 430b extend perpendicularly from the heads 428a, 428b. The members 430a, 430b may define gaps 438a, 438b between each. FIG. 4D shows a second sheet 442 that has been separated into sheet sections 442a, 442b. The sheet sections 442a, 442b may be shaped similarly to the sheet sections 440a, 440b. Each sheet section 442a, 442b may include a head 428c, 428d and members (e.g., fingers) 430c, 430d extending from the head. In some cases, the members 430c, 430d extend perpendicularly from the heads 428c, 428d, as shown in FIG. 4D. The members 430c, 430d may define gaps 438c, 438d between each member.

Figure 4E:
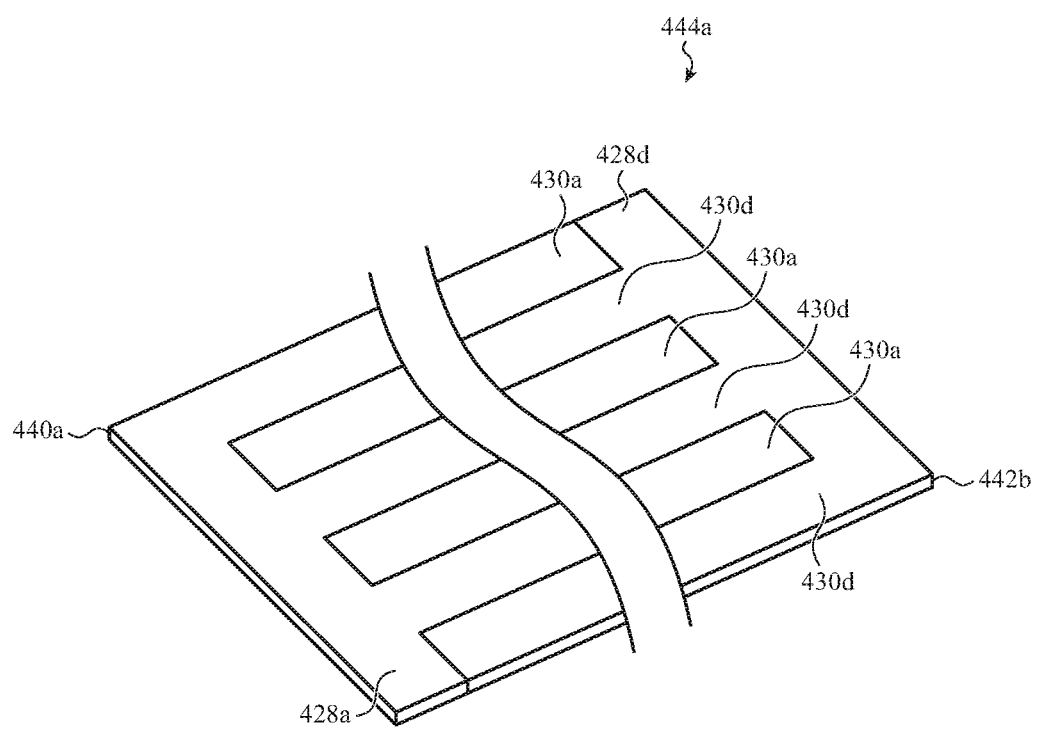
Figure 4F:
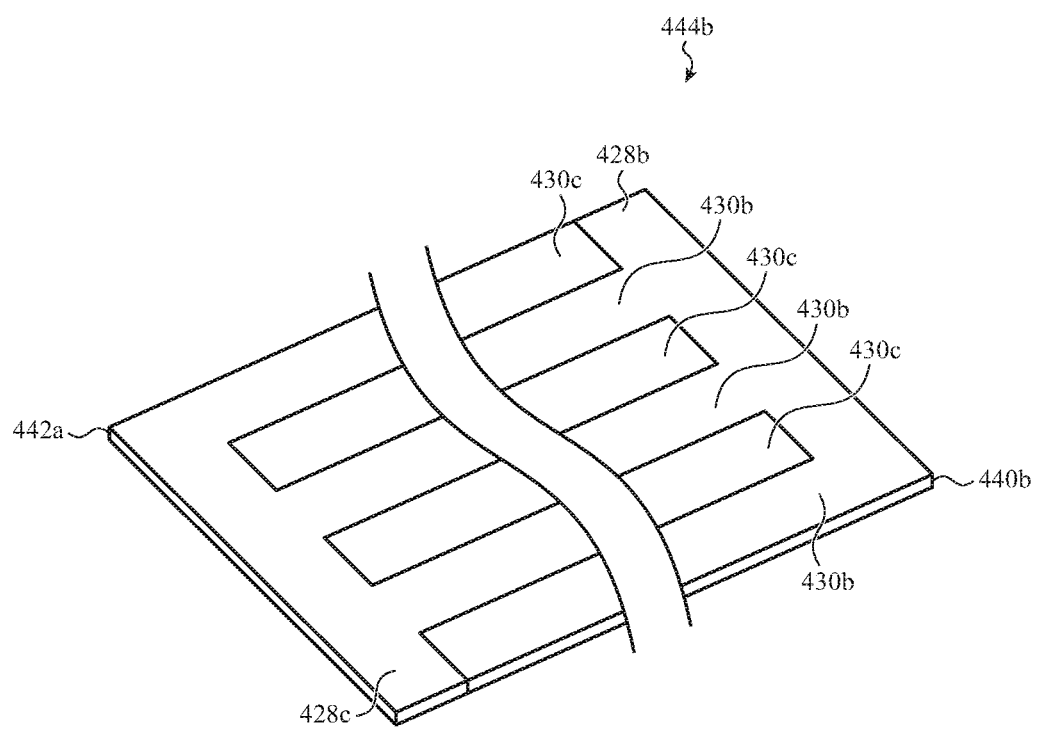

At block 308 of FIG. 3, the first sheet section of the first sheet is interdigitated with a third sheet section of a second sheet to form a combined sheet with multiple laterally adjacent substrates on the same layer. For example, as shown in FIG. 4E, the sheet section 440a may be interdigitated with the sheet section 442b to form a combined sheet 444a. In some cases, the second sheet section of the first sheet is interdigitated with a fourth sheet section of the second sheet (or another sheet) to form an additional combined sheet. For example, as shown in FIG. 4F, the sheet section 440b may be interdigitated with the sheet section 442a to form a combined sheet 444b. The heads 428a and 428b may simplify the manufacturing and assembly process by maintaining the alignment of the fingers defining the members 430a, 430b and maintaining the gaps between the fingers to make interdigitating the fingers easier. As discussed below, in some cases, the heads 428a and 428b may be removed from the layered sensor, for example by cutting the layered sensor during or after manufacturing.

The members and gaps of the sheet sections 440a, 440b, 442a, 442b may be shaped such that the sheet sections can be interdigitated with one another and form a continuous top and/or bottom surface of the combined sheets 444a, 444b. For example, as shown in FIG. 4E, each of the gaps 438a in the sheet section 440a may have a length and/or a width that is approximately the same as a length and/or a width of a respective member (e.g., finger) 430d of the sheet section 442b. Similarly, each of the members (e.g., fingers) 430a of the sheet section 440a may have a length and/or a width that is approximately the same as a length and/or a width of a respective gap 438d of the sheet section 442b. In some cases, the sheet section 442a has a shape that is approximately the same as a shape of the sheet section 440a, and/or the sheet section 442b has a shape that is approximately the same as a shape of the sheet section 440b. In some cases, the shape of the sheet section 442a is different from the shape of the sheet section 440a, and/or the shape of the sheet section 442b is different from the shape of the sheet section 440b.

The sheet 442 may be formed from similar or different materials as the sheet 440. For example, in some cases, the sheet 440 includes a piezoelectric material and the sheet 442 does not include a piezoelectric material. The sheet 442 may have similar or different electrodes as the sheet 440, or the sheet 442 may not include electrodes. For example, in some cases, the electrodes of the sheet 440 include silver and the electrodes of the sheet 442 do not include silver. The electrodes of the sheet 442 may have different dimensions as the electrodes of the sheet 440 and/or there may be more or fewer electrodes on the sheet 442 compared to the sheet 440. As such, different members of the combined sheets 444a, 444b may include different materials and/or different electrodes.

Figure 4G:
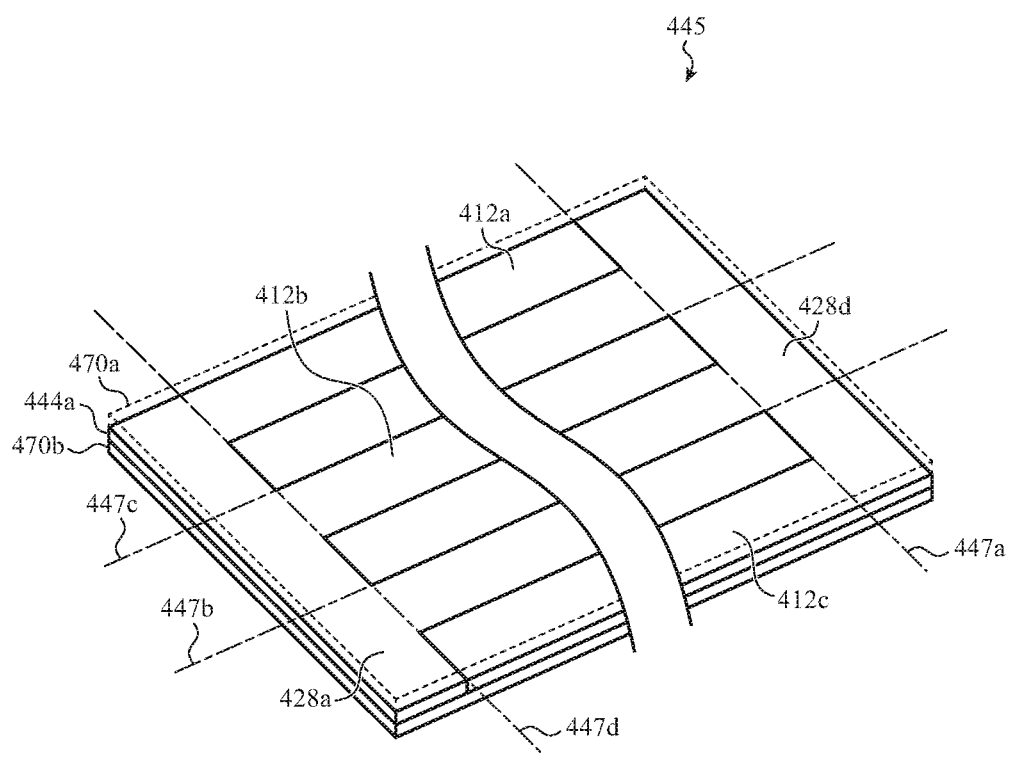

At block 310 of FIG. 3, the combined sheet is attached to one or more additional sheets to form a stack. For example, as shown in FIG. 4G, the combined sheet 444a may be positioned above, below, and/or between one or more additional sheets 470a, 470b such as one or more additional substrate layers and/or one or more ground layers. The sheets 444a, 470a, and 470b may form a stack 445. In some cases, the stack may be separated into multiple layered sensors (e.g., to be incorporated into a single sleep monitor or multiple sleep monitors).

Figure 4H:
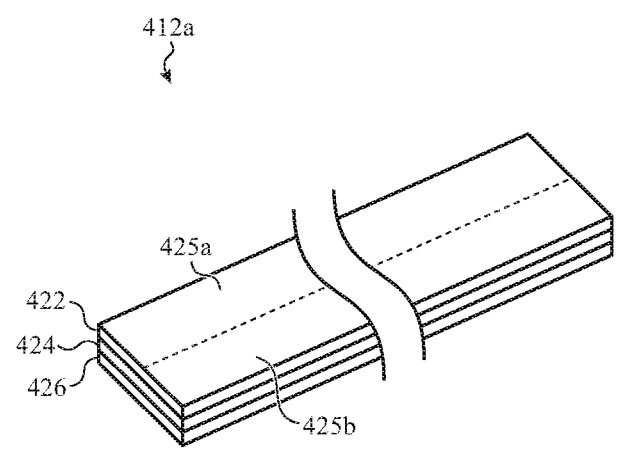

At block 312 of FIG. 3, the stack is cut and separated to form one or more layered sensors. For example, as shown in FIG. 4G, the stack 445 may be cut along cutting paths 447a, 447b, 447c, and 447d to form multiple layered sensors 412a, 412b, 412c. In some cases, cutting the stack 445 includes removing the heads 428a, 428d from the combined sheet (e.g., by cutting along cutting paths 447a and 447d). As shown in FIG. 4H, the flexible sensor 412a includes a layer 422 (shown in phantom; similar to layer 222 of FIG. 2), layer 424 (similar to layer 224 of FIG. 2), and layer 426 (similar to layer 226 of FIG. 2). One or more of the layers 422, 424, 426 may include multiple substrates in the same layer. For example, the layer 424 may include a first substrate 425a (similar to the substrate 225a of FIG. 2) from the sheet section 440a of FIG. 4E and a second substrate 425b (similar to the substrate 225b of FIG. 2) from the sheet section 442b of FIG. 4E.

The method 300 is an example method for manufacturing of a layered sensor for a sleep monitor and is not meant to be limiting. Methods for providing manufacturing a layered sensor for a sleep monitor may omit and/or add steps to the method 300. Similarly, steps of the method 300 may be performed in different orders than the example order discussed above. Additionally, steps of the method 300 are not limited to layered sensors for sleep monitors, and may be used to manufacture layered sensors or other components for a variety of applications, including electronic devices.

In some cases, the sheets used to form the interdigitated combined sheets discussed with respect to FIGS. 3-4H may include a single layer or multiple layers. In some cases, the sheets may include one or more support layers, adhesive layers, or the like. The support layers and/or adhesive layers may provide advantages, including simplifying the manufacturing process by making separating and/or interdigitating the sheet sections easier.

Figure 5A:
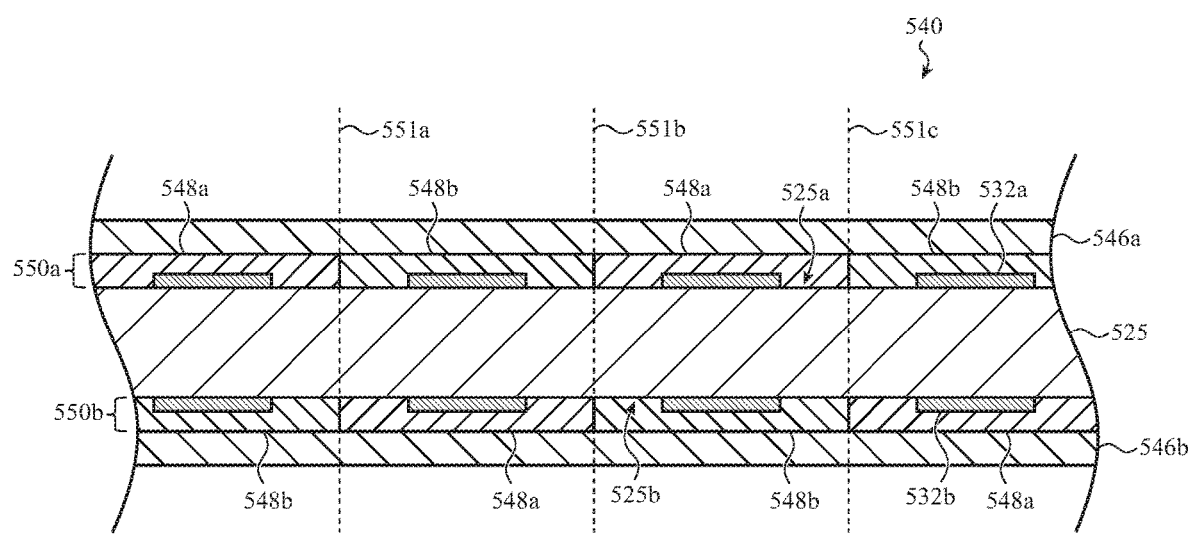
FIGS. 5A-5C show cross-section views of an example sheet, taken through section line B-B of FIG. 4A.
Figure 5B:
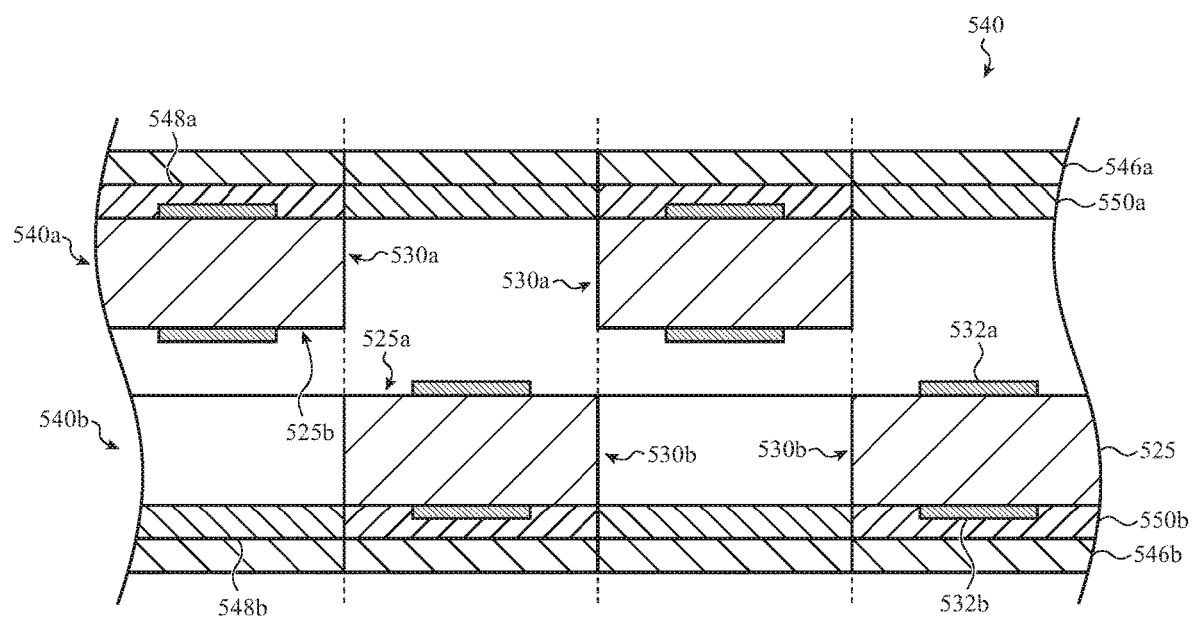
Figure 5C:
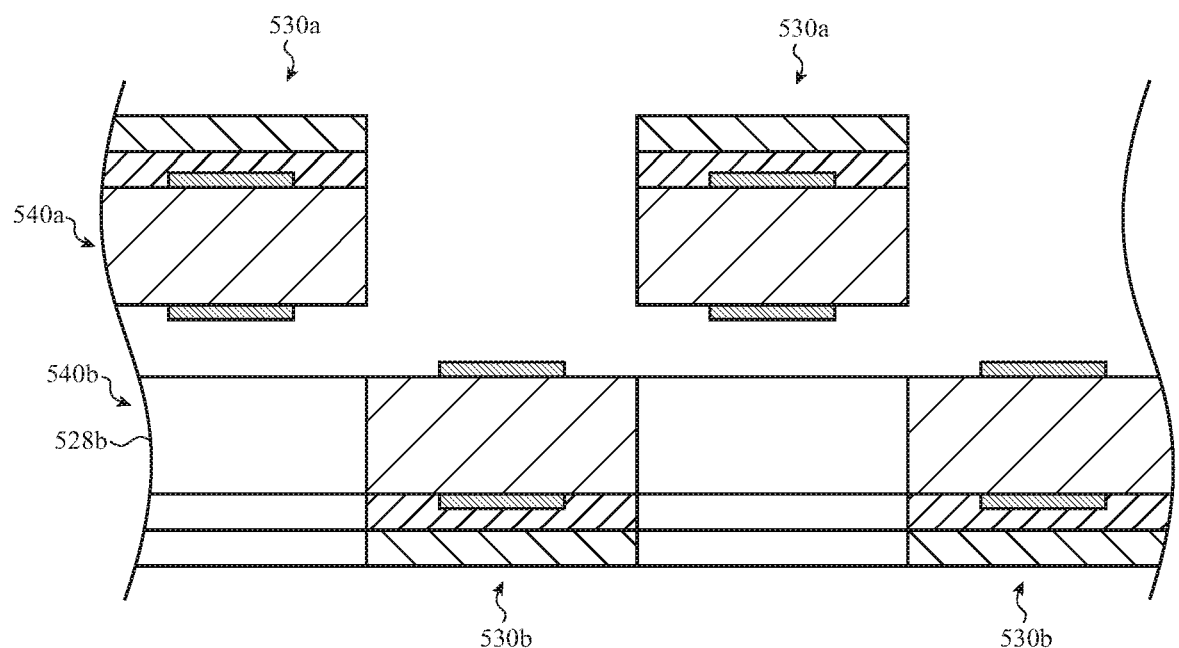

In some cases, the adhesive layer(s) include alternating regions corresponding to fingers of the sheet sections. The alternating regions may have different adhesive strength from one another to facilitate separating the sheet sections of a sheet. FIGS. 5A-5C show cross-section views of an example sheet 540, taken through section line B-B of FIG. 4A, including first and second adhesive layers with alternating regions having different adhesive strength from one another to facilitate separating sheet sections of the sheet. The sheet 540 may be similar to the sheet 440 discussed with respect to FIGS. 4A-4F.

As shown in FIG. 5A, the sheet 540 may include a substrate layer 525 (e.g., a PVDF substrate layer) defining a top surface 525a and a bottom surface 525b. The sheet 540 may include one or more electrodes 532a, 532b disposed on the top surface 525a and/or the bottom surface 525b of the substrate layer 525. In some embodiments, the electrodes 532a, 532b may be disposed at least partially within the substrate layer 525 (e.g., beneath the top surface 525a and/or the bottom surface 525b). The sheet 540 may additionally include a support layer 546a attached to the top surface 525a of the substrate layer 525 and/or a support layer 546b attached to the bottom surface 525b of the substrate layer 525. The sheet 540 may include adhesive layers 550a and 550b that attach the support layers 546a and 546b, respectively, to the substrate layer 525. Alternatively or additionally, the adhesive layers 550a and/or 550b may attach support layers 546a and/or 546b to the electrodes 532a and/or 532b.

As noted above, the adhesive layers 550a, 550b may include different regions having different properties, including adhesive strength. As noted above, as used herein, the term "adhesive strength" may refer to the ability of an adhesive (or another material) to adhere (e.g., stick) to a surface and bond surfaces together, such as the ability of an adhesive layer 550a, 550b to adhere to a substrate layer 525 and/or a support layer 546a, 546b. A material (e.g., an adhesive) having a higher adhesive strength means that the material adheres better compared to a material with a lower strength. Measures of adhesive strength may include tack (e.g., how quickly a bond is formed by a pressure-sensitive adhesive) and peel (e.g., the force needed to break the bond between an adhesive and a surface it has been applied to). For example, as shown in FIG. 5A, the adhesive layers 550a, 550b may include alternating regions 548a and 548b. In the example of FIG. 5A, the regions 548a have an adhesive strength that is higher than an adhesive strength of the regions 548b, but the reverse may be true in other embodiments.

As part of the process of forming a layered sensor having multiple laterally adjacent substrates on a single layer, the sheet 540 may be cut into a first sheet section and a second sheet section (or more than two portions), as described in more detail with respect to FIGS. 3 and 4A-4F. Cutting the sheet 540 may include making cuts at locations 551a, 551b, and 551c shown in FIG. 5A to form interdigitated members as discussed above. As shown in FIG. 5A, the boundaries between the alternating regions 548a, 548b of the adhesive layers 550a, 550b may at least approximately correspond to the cut locations 551a, 551b, 551c so that the alternating regions of the adhesive layers at least approximately correspond to the interdigitated members of the sheet once it is cut. As a result, each member may include one region of the adhesive layer along the top surface 525a of the substrate layer 525 and one region along the bottom surface 525b of the substrate layer 525. For each member the region of the adhesive layer that is positioned along the top surface 525a of the substrate layer 525 may have different properties (e.g., adhesive strength) than the region of the adhesive layer that is positioned along the bottom surface 525b of the substrate layer such that the substrate layer may be more easily separated from one region than the other. For example, as shown in FIG. 5A, a region 548a having a first adhesive strength may be positioned along the top surface 525a opposite a region 548b having a second adhesive strength less than the first adhesive strength.

FIG. 5B shows the sheet 540 cut into a first sheet section 540a that includes members (e.g., fingers) 530a and a second sheet section 540b that includes members (e.g., fingers) 530b. FIG. 5B shows the sheet sections 540a, 540b separated from one another. As shown in FIG. 5B, the bottom surfaces 525b of the substrate layer 525 (and the electrodes 532b) of each of the members 530a have separated from the corresponding regions 548b of the adhesive layer 550b. Similarly, the top surfaces 525a of the substrate layer 525 (and the electrodes 532a) of each of the members 530b have separated from the corresponding regions 548b of the adhesive layer 550a. The top surfaces 525a of the substrate layer 525 (and the electrodes 532a) of each of the members 530a remain adhered to the corresponding regions 548a of the adhesive layer 550a, and the bottom surfaces 525b of the substrate layer 525 (and the electrodes 532b) of each of the members 530b remain adhered to the corresponding regions 548a of the adhesive layer 550b. As such, each of the sheet sections 540a, 540b remains attached to a support layer 546a, 546b.

The support layers 546a, 546b may provide rigidity and other structural support to the members 530a, 530b so that they may maintain their shape during manufacturing. For example, the support layers 546a, 546b may allow the sheet sections 540a, 540b to maintain shapes similar to the shapes of the sheet sections 440a, 440b shown in FIG. 4C as they are handled or otherwise manipulated, and so that they may be interdigitated with one or more additional sheet sections. As shown in FIG. 5C, the portions of the support layers 546a, 546b and the adhesive layers 550a, 550b between the members 530a, 530b may be removed as part of the cutting and separation of the sheet sections 540a, 540b. This may allow the sheet sections 540a, 540b to be interdigitated with other sheet sections. In some cases, the support layers 546a, 546b and/or the adhesive layers 550a, 550b are removed from the members after the sheet sections 540a, 540b have been interdigitated with other sheet sections. In other cases, the support layers 546a, 546b and/or the adhesive layers 550a, 550b remain as part of combined sheets after the sheet sections 540a, 540b have been interdigitated with other sheet sections.

Figure 6A:
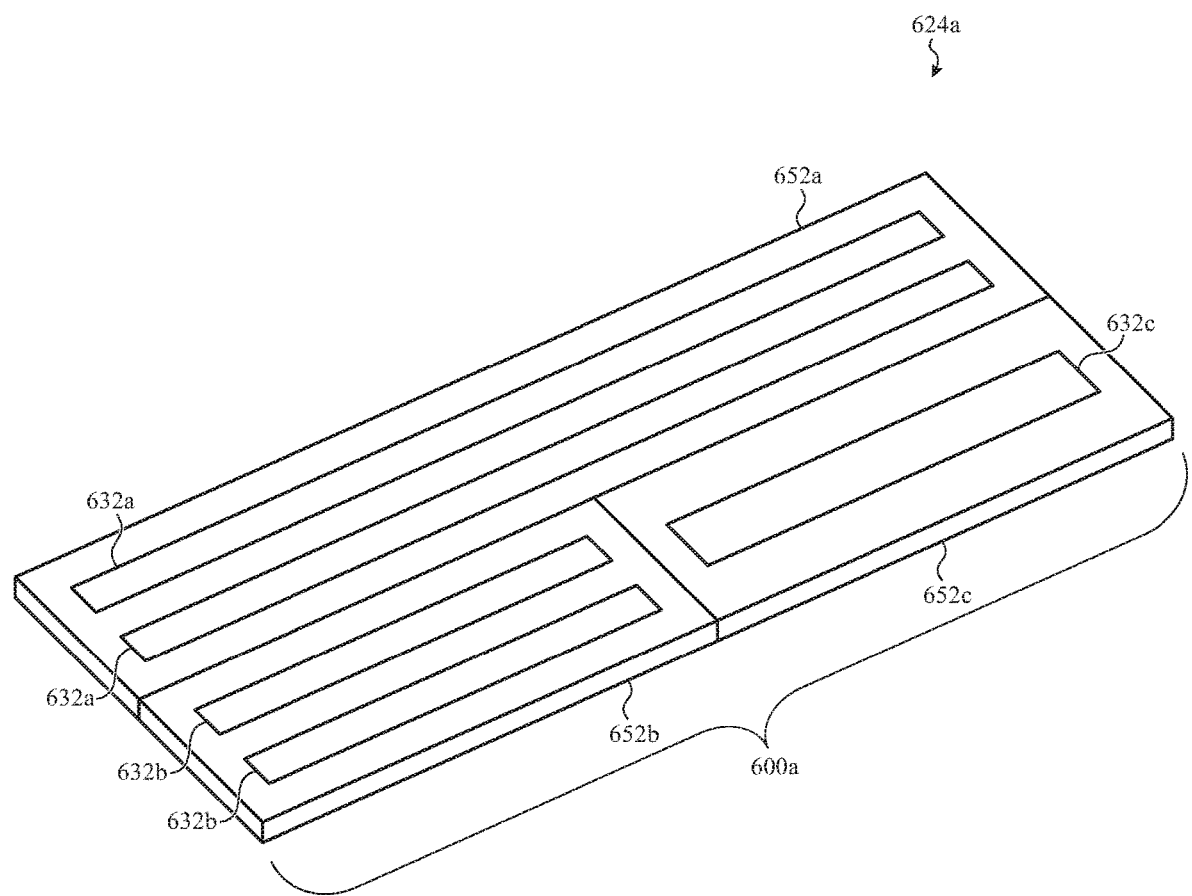
FIGS. 6A-6C show example arrangements of substrate layers having multiple substrates.
Figure 6B:
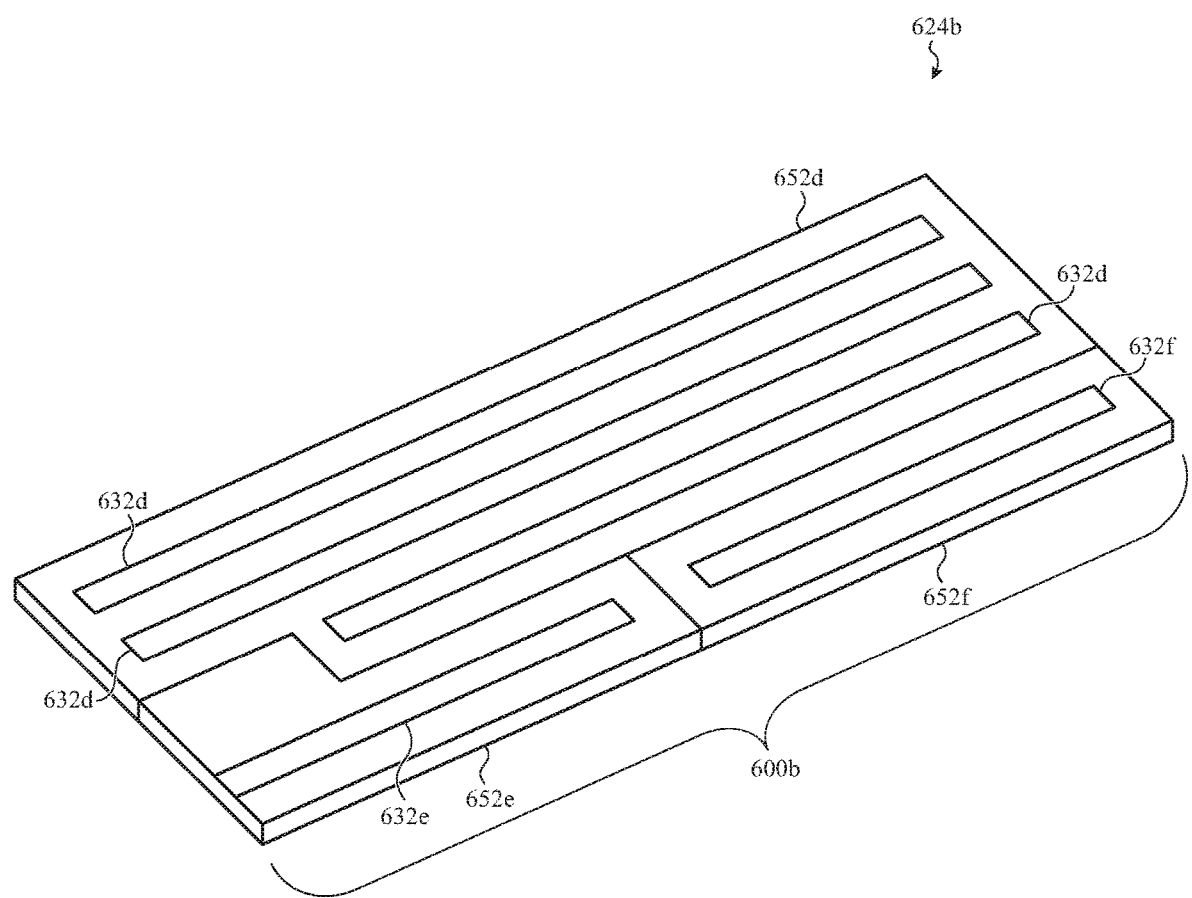
Figure 6C:
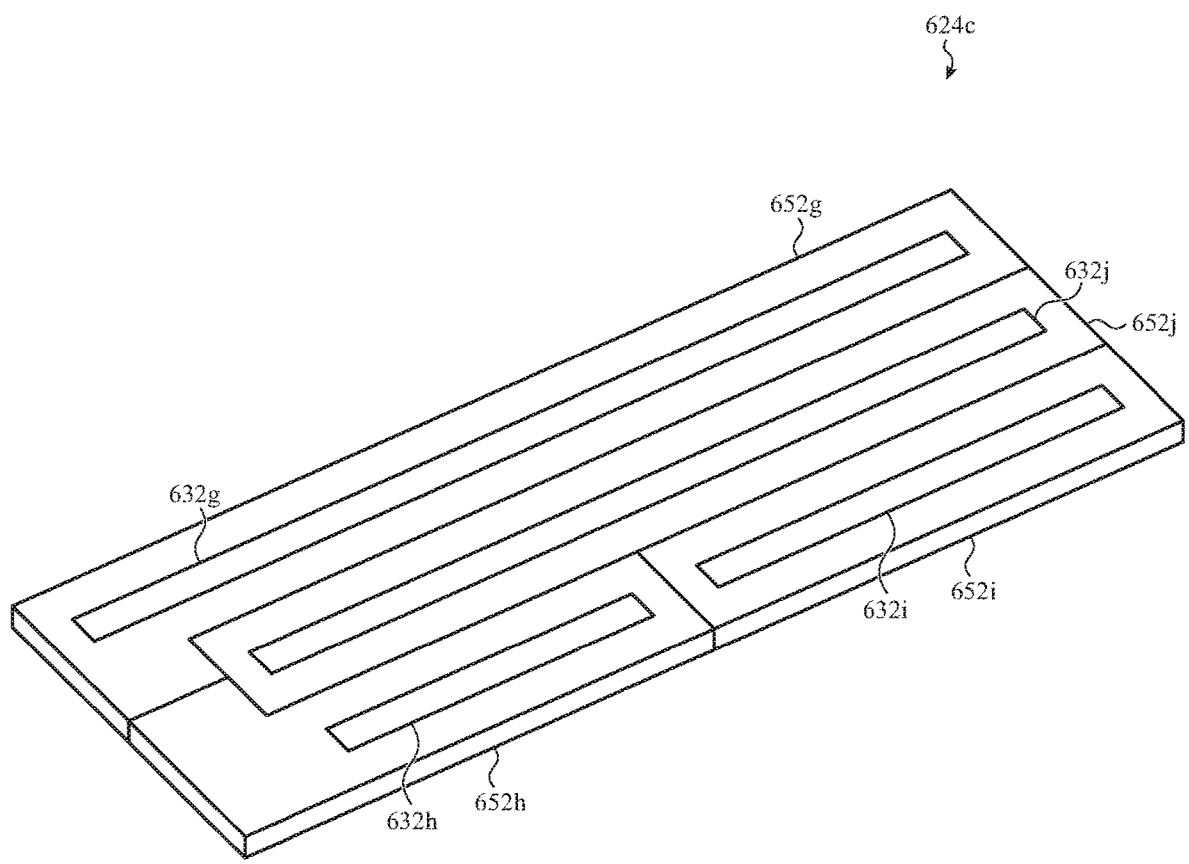

The substrate layers described herein may include different or additional features and/or structures than the example embodiments discussed with respect to FIGS. 2-5C. For example, while the substrate layers discussed with respect to FIGS. 2-5C may include members that are interdigitated with one another during a manufacturing or assembly process, this is not required, and substrate layers may have different arrangements and structures. Similarly, while substrate layers formed from two sheet sections have been discussed with respect to FIGS. 2-5C, in practice, substrate layers may be formed from any number of sheet sections arranged in any suitable way. FIGS. 6A-6C show example arrangements of substrate layers.

FIG. 6A shows a substrate layer 624a of a layered sensor that includes a first substrate 652a with electrodes 632a along a surface, a second substrate 652b with electrodes 632b along a surface, and a third substrate 652c with an electrode 632c along a surface. FIG. 6B shows a substrate layer 624b of a layered sensor that includes a first member 652d with electrodes 632d along a surface, a second member 652e with an electrode 632e along a surface, and a third member 652f with electrode 632f along a surface. FIG. 6C shows a substrate layer 624c of a layered sensor that includes a first member 652g with an electrode 632g along a surface, a second member 652h with an electrode 632h along a surface, a third member 652i with an electrode 632i along a surface, and a fourth member 652j with an electrode 632j along a surface.

The substrates included in a layered sensor may differ from one another. The size (e.g., length, width, thickness), shape, and/or materials of the members in each layer of a layered sensor may differ from one another. For example, as shown in FIG. 6A, the substrate 652a extends along an entire length 600a of the substrate layer, while the substrates 652b and 652c do not. As shown in FIG. 6B, a first portion of the substrate 652d may extend along an entire length 600b of the substrate layer and a second portion of the substrate 652d may not extend along the entire length 600b. As shown in FIG. 6C, one or more substrates (e.g., substrates 652g, 652h, 652i) may cooperate to at least partially surround one or more substrates (e.g., substrate 652j). In some cases, one or more of the substrates of a substrate layer may include PVDF, and one more of the members may not include PVDF.

The electrodes included along a substrate layer may differ from one another. The size (e.g., length, width, thickness), positioning, shape, or other properties (e.g., materials) of the electrodes may differ across different substrates or along a single substrate. As shown in FIG. 6A, the substrates 652a and 652b may include two electrodes (e.g., two parallel electrodes) on their surface, and the substrate 652c includes a single electrode on its surface. As shown in FIG. 6A, the electrode 632c may be wider and/or shorter than other electrodes. As shown in FIG. 6B, an electrode 632d of the substrate 652d may be shorter than other electrodes 632d of the substrate 652d. As shown in FIG. 6B, the electrode 632e may extend to an edge of the substrate 652e, while one or more additional electrodes of the substrate layer 624b may not extend to an edge of a substrate.

Figure 7:
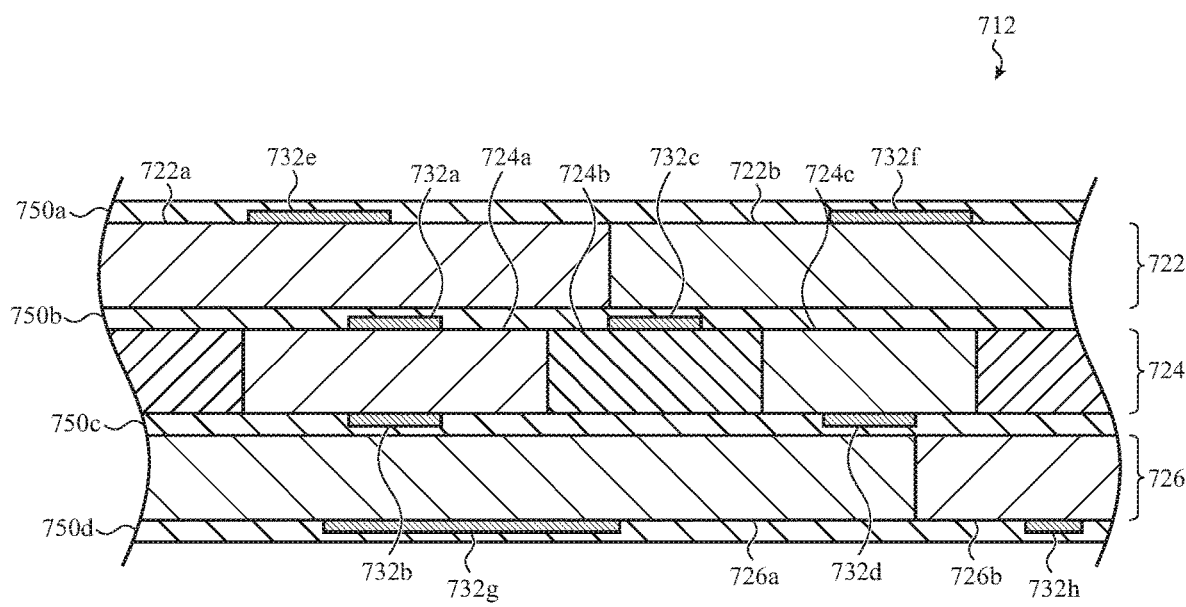
FIG. 7 shows a cross-section view of an example layered sensor of a sleep monitor, taken through section line A-A of FIG. 1B.

As noted above, the substrates included in a substrate layer (or other layers of a layered sensor) may differ from one another. FIG. 7 shows a cross-section view of an example layered sensor 712 of a sleep monitor, taken through section line A-A of FIG. 1B. As shown in FIG. 7, the layered sensor may include substrates, electrodes, adhesive layers, and other components of different sizes (e.g., length, width, thickness), shapes, and/or materials. The layers 722, 724, 726 may be formed by interdigitating two or more sheet sections as described herein. The layers 722, 724, 726 may include substrates (e.g., fingers) 722a, 722b, 724a, 724b, 724c, 726a, 726b similar to the substrates described herein. As shown in FIG. 7, the widths and/or positions of the substrates of the layers 722, 724, 726 may be different compared to other substrates in the same layer or other layers. For example, the substrate 724a of layer 724 is wider than the substrate 724b of layer 724. The layered sensor may include electrodes 732a, 732b, 732c, 732d, 732e, 732f, 732g, 732h similar to those described herein. The electrodes may have different widths, thicknesses, materials, and the like compared to other electrodes along the same layer or other layers. For example, the electrode 732g positioned along the layer 726 may have a different width than the electrode 732h positioned along the layer 726.

Figure 8A:
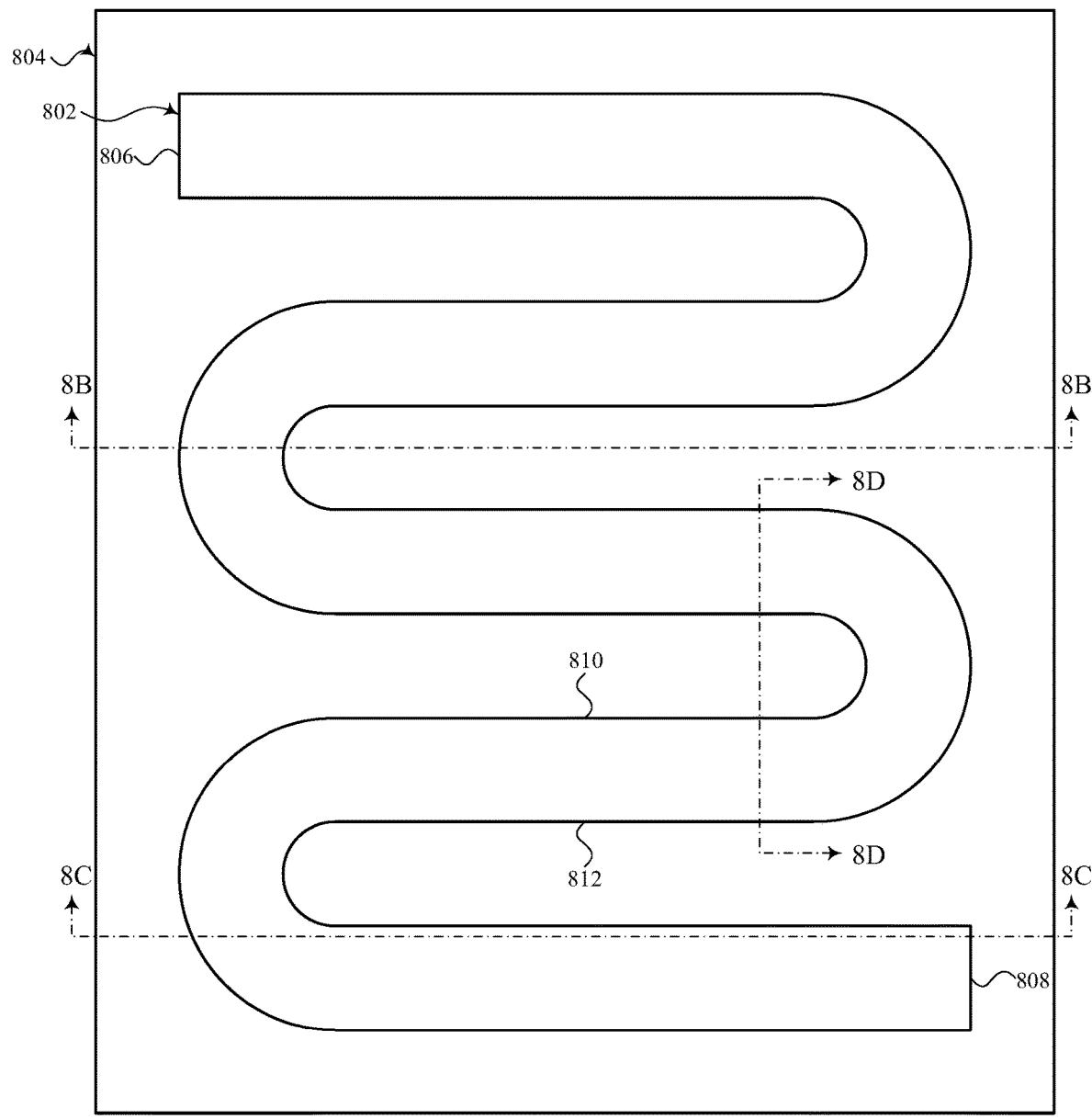
FIGS. 8A-8D show another example of a layered sensor having laterally adjacent substrates in a single layer.
Figure 8B:
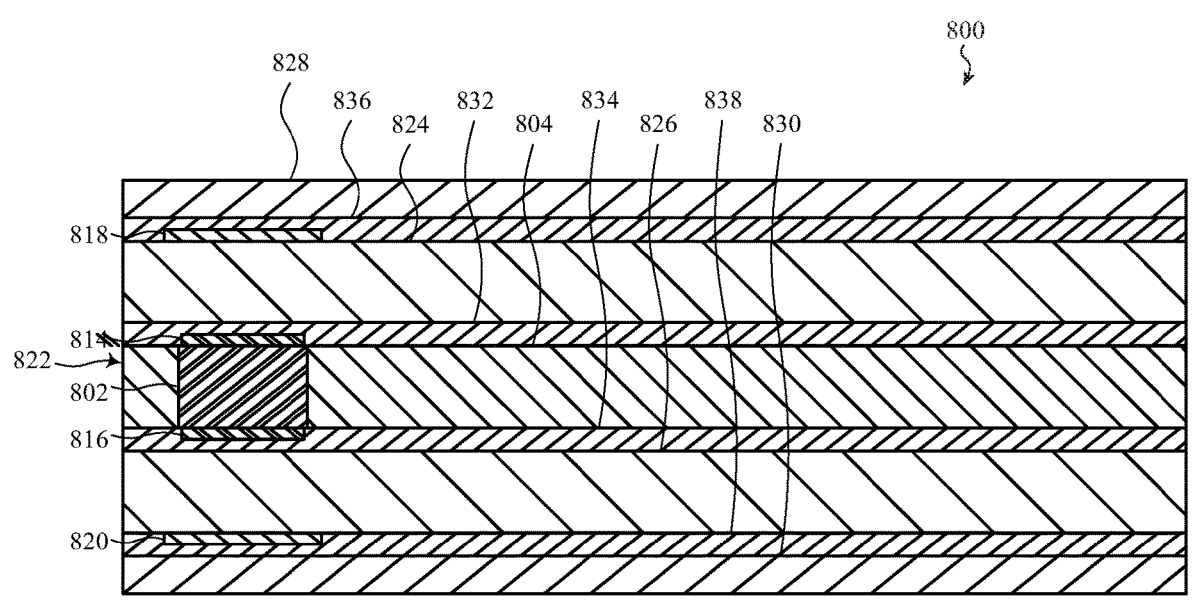
Figure 8C:
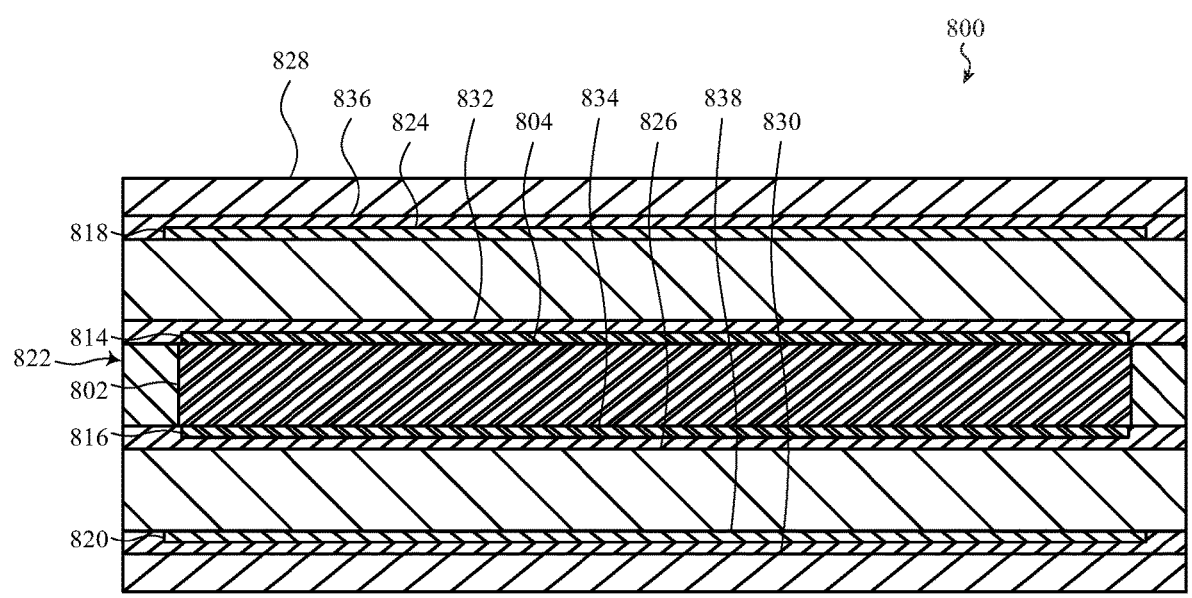
Figure 8D:
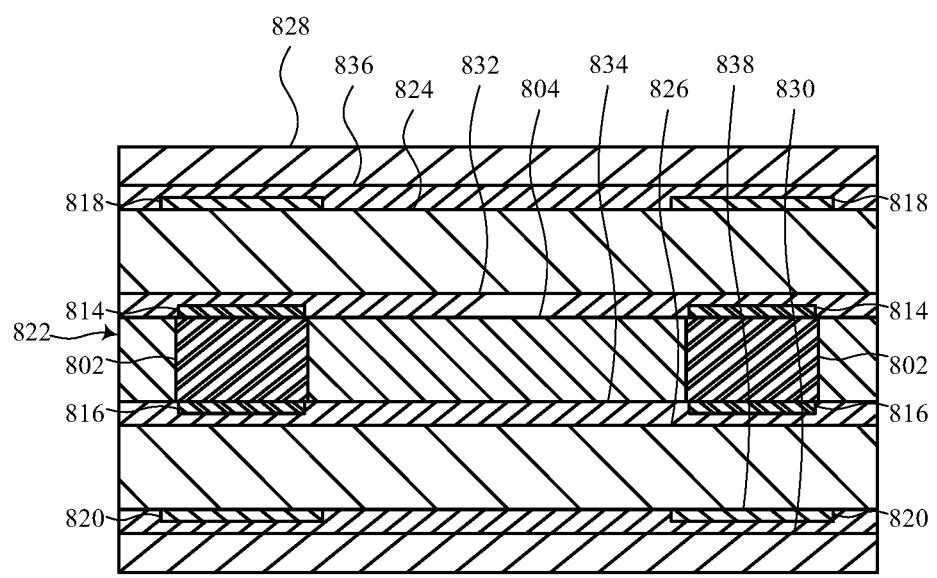

FIGS. 8A-8D show another example of a layered sensor 800 having laterally adjacent substrates in a single layer. FIG. 8A shows a plan view of the layered sensor 800, and FIGS. 8B-8D show various cross-sections of the layered sensor 800. The layered sensor 800 may be able to flex more than a layered sensor having a PVDF substrate and associated electrodes that extend in a straight line, and may respond to high strain with low stress.

As shown in FIG. 8A, one or more of the laterally adjacent substrates included in the single layer may have a serpentine shape, or at least one serpentine-shaped edge. For example, a first substrate 802 may have a serpentine shape, and a second substrate 804 may define a negative of the serpentine shape (i.e., a cutout) and have serpentine-shaped edges. Alternatively, one or more of the laterally adjacent substrates 802, 804 may have a curved or arcuate shape or curved or arcuate-shaped edge. In some cases, the entirety of a substrate may have a serpentine shape (or a curved or arcuate shape), or define a negative of a serpentine, curved, or arcuate shape, or have at least one serpentine, curved, or arcuate-shaped edge. In other cases, only a portion of a substrate, or only a portion of an edge, may be serpentine, curved, or arcuate-shaped. Although the lateral edges of the serpentine-shaped first substrate 802 is shown to be entirely surrounded by the second substrate 804 in FIG. 8A, one or both ends 806, 808 of the first substrate 802, or one or more portions along the serpentine-shaped edges of the first substrate 802, may not be surrounded by the second substrate 804. Additionally or alternatively, the second substrate 804 may have interior edges that are separated from one or more ends 806, 808 or edges 810, 812 of the first substrate 802 by a lateral gap. For example, instead of the interior edges of the second substrate 804 closely abutting (i.e., contacting) the ends 806, 808 and edges 810, 812 of the first substrate 802, one or more interior edges of the second substrate 804 may be separated from the ends 806, 808 or edges 810, 812 of the first substrate 802 by a lateral gap (e.g., a lateral gap having a width that is 1% or less, up to 10%, or up to 20% of the width of the first substrate 802, or even a larger lateral gap).

In some cases, a set of one or more substrates may be disposed at different lateral positions around the first substrate 802. For example, when the first and second ends 806, 808 of the first substrate 802 are not surrounded by a laterally adjacent substrate, a third substrate may be disposed laterally adjacent a first serpentine-shaped edge 810 of the first substrate 802, and a fourth substrate may be disposed laterally adjacent a second serpentine-shaped edge 812 of the first substrate 802. In some cases, one or more of a number of laterally adjacent substrates may have a generally serpentine, curved, or arcuate-shaped edge on which another pattern is superimposed. The other pattern may be an intentional pattern or, for example, may be an unintended or unavoidable byproduct of a cutting or machining process.

In the example shown, and as previously discussed, the first substrate 802 has a serpentine shape, and the second substrate 804 has a cutout that defines, or substantially defines, a negative of the first substrate's serpentine shape. In some embodiments, the first substrate 802 may include a flexible piezoelectric material (e.g., the first substrate 802 may be a PVDF substrate), and the second substrate 804 may be a dielectric substrate (e.g., a PU, TPU, or SMP substrate).

The first and second substrates 802, 804 may be disposed laterally adjacent one another, in a single layer. An electrode 814 or 816 may be disposed on one or each planar surface of the first substrate 802, as shown in FIGS. 8B-8D. In some cases, each of the electrodes 814, 816 may have a serpentine, curved, or arcuate shape having a width that is the same as, or similar to (e.g., up to 1%, 10%, or 20% wider than or narrower than), the width of the first substrate 802. By way of example, the electrodes 814, 816 are shown to have widths that are narrower than the width of the first substrate 802. In other examples, the electrodes 814, 816 may have shapes that do not correspond to the shape of the first substrate 802. However, this may generate stray capacitance or other noise effects in a signal read from the electrode(s) 814, 816. In some cases, the electrodes 814, 816 may be formed of silver. The electrodes may alternatively be formed of other conductive materials (e.g., metals) or combinations of materials. In some embodiments, the electrodes 814, 816 may be electrically connected to respective first and second inputs of a differential sensor. In some embodiments, a differential signal provided by the electrodes 814, 816 may be received by a processing unit and used to determine a sleep characteristic of a user.

An electrical shield component 818 or 820 may be disposed over, and spaced apart from, each electrode 814, 816 (i.e., with each electrode 814, 816, when present, disposed between the first substrate 802 and a respective electrical shield component 818, 820). In some cases, each of the electrical shield components 818, 820 may have a serpentine, curved, or arcuate shape having a width that is the same as, or similar to (e.g., up to 1%, 10%, or 20% wider than or narrower than), the width of the first substrate 802. By way of example, the electrical shield components 818, 820 are shown to have widths that are wider than the widths of the first substrate 802 and electrodes 814, 816. In other examples, the electrical shield components 818, 820 may have shapes that do not correspond to the shapes of the first substrate 802 or electrodes 814, 816. For example, the electrical shield components 818, 820 may cover the first substrate 802 and all or a substantial portion (e.g., up to 50%, 75%, 90%, or 100%) of the second substrate 804. In some examples, an electrical shield component 818 or 820 may include aluminum (Al) and/or copper (Cu), and/or another metal, sputtered on a PU, TPU, and/or SMP substrate. An electrical shield component 818, 820 may also be provided by a conductive fabric.

FIG. 8B shows a first cross-section of the layered sensor 800, taken along line 8B-8B of FIG. 8A. The cross-section extends perpendicularly to a meandering length of the serpentine-shaped first substrate 802. As shown, the layers of the layered sensor 800 may include a layer 822 that includes the first and second substrates 802, 804.

The layered sensor 800 may also include one or more intermediate layers, or support layers, on or between which the electrodes 814, 816, electrical shield components 818, 820, and/or other components are disposed. For example, the layered sensor 800 may include first and second intermediate layers 824, 826 (e.g., dielectric layers having the same or different composition as the second substrate 804 (e.g., PU, TPU, or SMP compositions). One of the electrical shield components 818 or 820 may be disposed on a respective one of the first or second intermediate layers 824, 826, with the first intermediate layer 824 being disposed between the first electrode 814 and the first electrical shield component 818, and with the second intermediate layer 826 disposed between the second electrode 816 and the second electrical shield component 820.

In some embodiments, the first and second electrical shield components 818, 820 may define the outmost layers of the layered sensor 800. In other embodiments, an exterior dielectric layer (or other protective layer that protects the layered sensor 800 and/or a user) 828 or 830 may be attached to each intermediate layer 824, 826, with the first intermediate layer 824 disposed between a first exterior dielectric layer 828 and the layer 822, and with the second intermediate layer 826 disposed between a second exterior dielectric layer 830 and the layer 822. In some cases, the first and second exterior dielectric layers 828, 830 may be formed of PU, TPU, or SMP.

A set of adhesive layers 832, 834 may adhere the intermediate layers 824, 826 to the single layer 822. and another set of adhesive layers 836, 838 may adhere the exterior dielectric layers 828, 830 to the intermediate layers 824, 826.

FIG. 8C shows a second cross-section of the layered sensor 800, taken along line 8C-8C of FIG. 8A. The cross-section extends parallel to the meandering length of the serpentine-shaped first substrate 802, and includes the same components and layers described with reference to FIG. 8B.

FIG. 8D shows a third cross-section of the layered sensor 800, taken along line 8D-8D of FIG. 8A. The cross-section extends perpendicularly to two different portions of the meandering length of the serpentine-shaped first substrate 802. The cross-section includes the same components and layers described with reference to FIG. 8B.

Figure 9A:
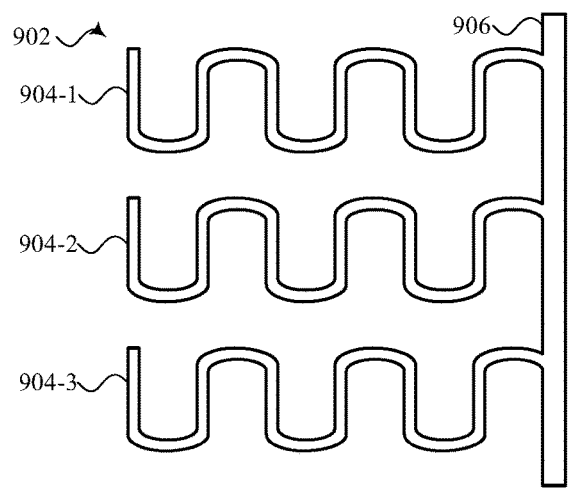
FIGS. 9A-9E illustrate an example set of operations for forming laterally adjacent substrates in a single layer for use in a layered sensor such as the layered sensor described with reference to FIGS. 8A-8D.

FIGS. 9A-9E illustrate an example set of operations for forming laterally adjacent substrates in a single layer, for use in a layered sensor such as the layered sensor described with reference to FIGS. 8A-8D. As shown in FIG. 9A, a first substrate 902 may be cut or patterned to form one or more serpentine, curved, or arcuate-shaped members 904-1, 904-2, 904-3. In the case of multiple members 904-1, 904-2, 904-3, the members 904-1, 904-2, 904-3 may be attached to a head 906 for ease of handling (e.g., the head 906 and members 904-1, 904-2, 904-3 may all be cut or patterned from the first substrate 902). In some cases, the first substrate 902 may be a PVDF substrate.

Figure 9B:
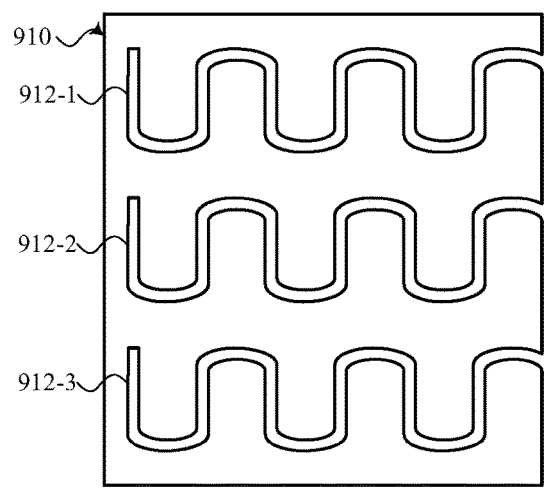

As shown in FIG. 9B, a second substrate 910 may be cut or patterned to form one or more serpentine, curved, or arcuate-shaped negatives 912-1, 912-2, 912-3 of the members 904-1, 904-2, 904-3 formed in the first substrate 902. In some cases, the second substrate 910 may be a PU, TPU, or SMP substrate.

Figure 9C:
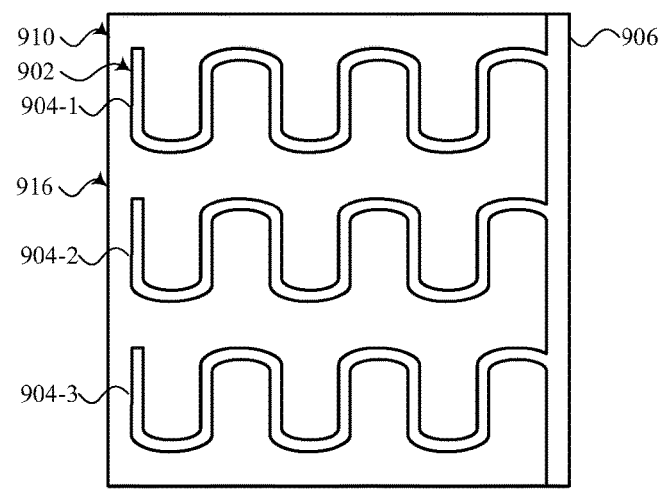

As shown in FIG. 9C, the cut or patterned first substrate 902 may be inset into the cut or patterned second substrate 910 (or vice versa), forming a single layer 916 with laterally adjacent substrates.

Figure 9D:
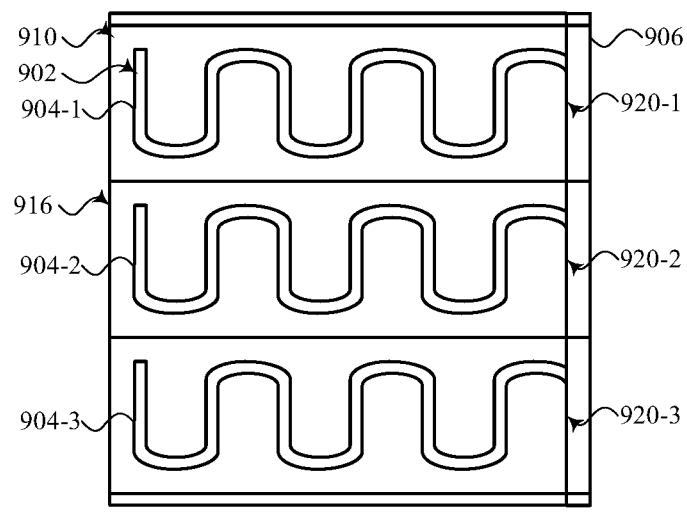
Figure 9E:
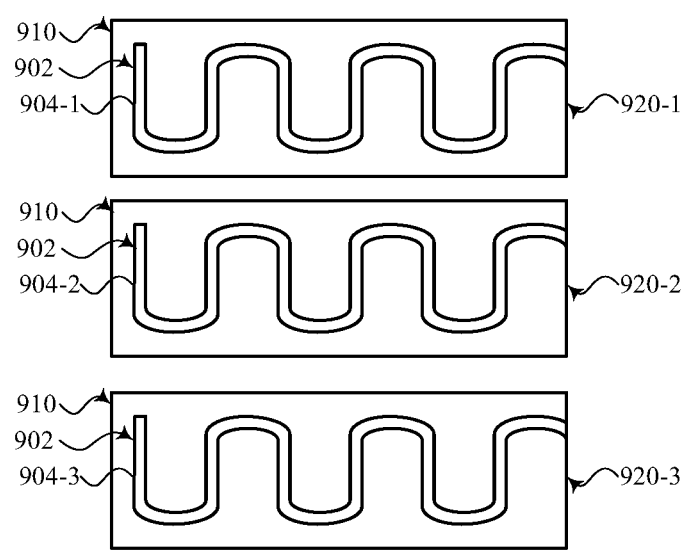

As shown in FIG. 9D, and if the first substrate 902 includes multiple members 904-1, 904-2, 904-3 intended for multiple sensors, the single layer 916 may be cut or otherwise divided into different devices, such as a first device 920-1, a second device 920-2, and a third device 920-3. Also, the head 906 may be cut or otherwise separated from the single layer 916. The separated devices 920-1, 920-2, 920-3 are shown in FIG. 9E.

In some embodiments, one or more electrodes may be formed on (or attached to) the first substrate 902, and/or one or more intermediate layers or support layers may be attached to the first substrate 902 (e.g., one or more intermediate layers supporting one or more electrical shield components) may be attached the single layer 916, and/or one or more exterior dielectric layers may be attached to the intermediate layers. Each of these operations may be performed before the first substrate 902 is cut or patterned, or after the first substrate is cut or patterned, or after the first substrate 902 and second substrate 910 are positioned laterally adjacent one another in the single layer 916. The single layer 916 may be cut or otherwise divided before or after one or more of the electrodes, electrical shield components, intermediate layers, adhesive layers, and/or other components or layers are formed or stacked on the single layer 916 having laterally adjacent substrates. In some embodiments, the single layer 916 may be attached to a carrier substrate before being cut or otherwise divided, to keep the devices divided from the single layer 916 in known positions with respect to one another while the devices are additionally processed.

In some cases, the layered sensor materials and/or layered sensor construction techniques described with reference to FIGS. 3, 4A-4H, and/or 5A-5C can be incorporated into the layered sensors and/or layered sensor construction operations described with reference to FIGS. 8A-9E.

The layered sensors described with reference to FIGS. 8A-9E, and/or the various layers and components thereof, are preferably formed of materials having a linear stress-strain curve within an intended operating range of the layered sensors (or at least PU, TPU, or SMP (e.g., POU) layers having a linear stress-strain curve). Materials having a linear stress-strain curve have no hysteresis. Although the layered sensors described with reference to FIGS. 8A-9E may also be formed using materials that do not have linear stress-strain curves, linear stress-strain curves eliminate hysteresis and provide a sensor that has the same linear response regardless of the direction that it flexes. In some cases, the materials may not have precisely linear stress-strain curves, and may therefore have some hysteresis. For example, the materials may have stress-strain curves that are within 5%, or within 10%, of linear.

A linear stress-strain curve within the intended operating range, in combination with a low modulus of elasticity within the intended operating range (e.g., a modulus of elasticity that is close to that of human skin), in combination with a serpentine-shaped first substrate (e.g., a serpentine-shaped sensing substrate, such as a PVDF substrate) can provide a layered sensor that matches (or approaches) the acoustic impedance of human skin. Matching (or approaching) the acoustic impedance of human skin can be important for effectively measuring cardiac and/or respiratory sounds of the human body.

Although the layered sensors described herein have been discussed in the context of an in-bed sensor, the layered sensors described herein may also be used in other contexts, such as: in a microphone; in a blood pressure cuff; in a shoe insole (e.g., as a weight distribution sensor); and so on.

Figure 10:
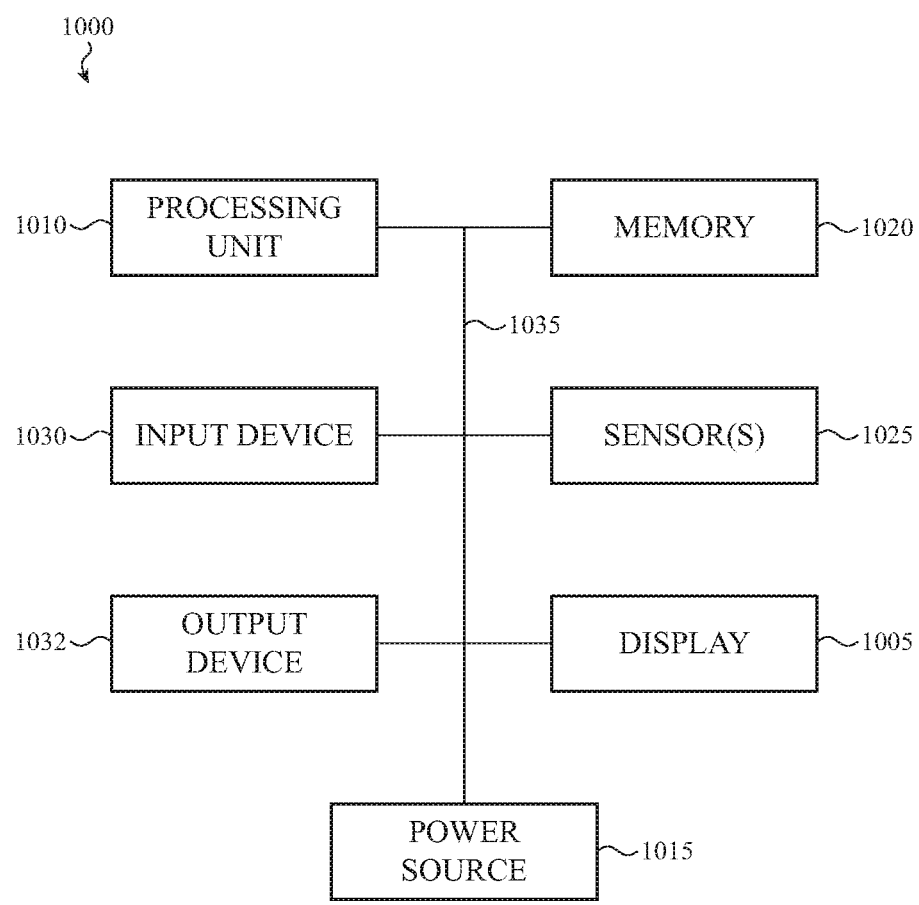
FIG. 10 shows a sample electrical block diagram of an electronic device that may incorporate and/or be connected to a sleep monitor having a layered sensor.

FIG. 10 shows a sample electrical block diagram of an electronic device 1000 that may incorporate and/or be connected to a sleep monitor having a layered sensor. The electronic device may in some cases take the form of any suitable electronic device, including sleep monitors as described herein, wearable electronic devices, timekeeping devices, health monitoring or fitness devices, portable computing devices, mobile phones (including smart phones), tablet computing devices, digital media players, virtual reality devices, audio devices (including earbuds and headphones), and the like. The electronic device 1000 can include a display 1005 (e.g., a light-emitting display), a processing unit 1010, a power source 1015, a memory 1020 or storage device, a sensor 1025, an input device 1030 (a sleep monitor), and an output device 1032.

The processing unit 1010 can control some or all of the operations of the electronic device 1000. The processing unit 1010 can communicate, either directly or indirectly, with some or all of the components of the electronic device 1000. For example, a system bus or other communication mechanism 1035 can provide communication between the processing unit 1010, the power source 1015, the memory 1020, the sensor 1025, and the input device(s) 1030, and the output device(s) 1032.

The processing unit 1010 can be implemented as any electronic device capable of processing, receiving, or transmitting data or instructions. For example, the processing unit 1010 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 1000 can be controlled by multiple processing units. For example, select components of the electronic device 1000 (e.g., a sensor 1025) may be controlled by a first processing unit and other components of the electronic device 1000 (e.g., the display 1005) may be controlled by a second processing unit, where the first and second processing units may or may not be in communication with each other. In some cases, the processing unit 1010 may determine a biological parameter of a user of the electronic device, such as an ECG for the user.

The power source 1015 can be implemented with any device capable of providing energy to the electronic device 1000. For example, the power source 1015 may be one or more batteries or rechargeable batteries. Additionally or alternatively, the power source 1015 can be a power connector or power cord that connects the electronic device 1000 to another power source, such as a wall outlet.

The memory 1020 can store electronic data that can be used by the electronic device 1000. For example, the memory 1020 can store electrical data or content such as, for example, audio and video files, documents and applications, device settings and user preferences, timing signals, control signals, and data structures or databases. The memory 1020 can be configured as any type of memory. By way of example only, the memory 1020 can be implemented as random access memory, read-only memory, Flash memory, removable memory, other types of storage elements, or combinations of such devices.

The electronic device 1000 may also include one or more sensors 1025 positioned almost anywhere on the electronic device 1000. The sensor(s) 1025 can be configured to sense one or more types of parameters, such as but not limited to, pressure, light, touch, heat, movement, relative motion, biometric data (e.g., biological parameters), and so on. For example, the sensor(s) 1025 may include a layered sensor as discussed above, a heat sensor, a position sensor, a light or optical sensor, an accelerometer, a pressure transducer, a gyroscope, a magnetometer, a health monitoring sensor, and so on. Additionally, the one or more sensors 1025 can utilize any suitable sensing technology, including, but not limited to, capacitive, ultrasonic, resistive, optical, ultrasound, piezoelectric, and thermal sensing technology. In some examples, the sensors 1025 may include one or more of the contact sensors, force sensors, and/or electrodes described herein (e.g., one or more electrodes in a layered sensor as described herein).

In various embodiments, the display 1005 provides a graphical output, for example, associated with an operating system, user interface, and/or applications of the electronic device 1000. In one embodiment, the display 1005 includes one or more sensors and is configured as a touch-sensitive (e.g., single-touch, multi-touch) and/or force-sensitive display to receive inputs from a user. For example, the display 1005 may be integrated with a touch sensor (e.g., a capacitive touch sensor) and/or a force sensor to provide a touch- and/or force-sensitive display. The display 1005 is operably coupled to the processing unit 1010 of the electronic device 1000.

The display 1005 can be implemented with any suitable technology, including, but not limited to, liquid crystal display (LCD) technology, light emitting diode (LED) technology, organic light-emitting display (OLED) technology, organic electroluminescence (OEL) technology, or another type of display technology. In some cases, the display 1005 is positioned beneath and viewable through a cover sheet that forms at least a portion of an enclosure of the electronic device 1000.

In various embodiments, the input devices 1030 may include any suitable components for detecting inputs. Examples of input devices 1030 include audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 1030 may be configured to detect one or more particular types of input and provide a signal (e.g., an input signal) corresponding to the detected input. The signal may be provided, for example, to the processing unit 1010.

As discussed above, in some cases, the input device(s) 1030 include a touch sensor (e.g., a capacitive touch sensor) integrated with the display 1005 to provide a touch-sensitive display. Similarly, in some cases, the input device(s) 1030 include a force sensor (e.g., a capacitive force sensor) integrated with the display 1005 to provide a force-sensitive display.

The output devices 1032 may include any suitable components for providing outputs. Examples of output devices 1032 include audio output devices (e.g., speakers), visual output devices (e.g., lights or displays), tactile output devices (e.g., haptic output devices), communication devices (e.g., wired or wireless communication devices), and so on, or some combination thereof. Each output device 1032 may be configured to receive one or more signals (e.g., an output signal provided by the processing unit 1010) and provide an output corresponding to the signal.

In some cases, input devices 1030 and output devices 1032 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 1010 may be operably coupled to the input devices 1030 and the output devices 1032. The processing unit 1010 may be adapted to exchange signals with the input devices 1030 and the output devices 1032. For example, the processing unit 1010 may receive an input signal from an input device 1030 that corresponds to an input detected by the input device 1030. The processing unit 1010 may interpret the received input signal to determine whether to provide and/or change one or more outputs in response to the input signal. The processing unit 1010 may then send an output signal to one or more of the output devices 1032, to provide and/or change outputs as appropriate.

As described above, one aspect of the present technology is the gathering and use of data available from various sources to provide variable frictional feedback, electrocardiograms, and the like. The present disclosure contemplates that, in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide electrocardiograms to the user and/or variable frictional feedback that is tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of variable frictional feedback and electrocardiograms or other biometrics, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, variable frictional feedback may be provided based on non-personal information data or a bare minimum amount of personal information, such as events or states at the device associated with a user, other non-personal information, or publicly available information.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A layered sensor for a flexible sleep monitor, comprising:
   a first flexible layer;
   a second flexible layer that is substantially parallel to the first flexible layer;
   a substrate layer positioned between the first flexible layer and the second flexible layer, and comprising:
      a first substrate formed of a first material, and configured to generate electric charge in response to a force applied to the flexible sleep monitor; and
      a second substrate formed of a second material different from the first material and positioned laterally adjacent to the first substrate;
   a first electrode disposed on a first surface of the first substrate; and
   a second electrode disposed on a second surface of the second substrate, wherein:
      the first surface and the second surface cooperate to define a continuous surface of the substrate layer;
      the substrate layer is flexible; and
      the first electrode and the second electrode are configured to be electrically coupled to a processing unit configured to determine a sleep characteristic using a signal received from at least one of the first electrode or the second electrode.

2. The layered sensor of claim 1, wherein:
   the continuous surface of the substrate layer is a first continuous surface of the substrate layer;
   the first flexible layer comprises a third substrate;
   the second flexible layer comprises a fourth substrate;
   the first continuous surface of the substrate layer faces a bottom surface of the first flexible layer;
   the substrate layer defines a second continuous surface opposite the first continuous surface and facing a top surface of the second flexible layer; and
   the layered sensor further comprises:
      a third electrode disposed on a third surface of the third substrate and configured to be electrically coupled to the processing unit; and
      a fourth electrode disposed on a fourth surface of the fourth substrate and configured to be electrically coupled to the processing unit.

3. The layered sensor of claim 2, wherein:
   the first flexible layer comprises a fifth substrate cooperating with the third substrate to define the bottom surface of the first flexible layer; and
   at least one of the first flexible layer or the second flexible layer is a ground layer.

4. The layered sensor of claim 1, wherein the substrate layer is formed by interdigitating fingers of a first sheet comprising the first substrate with fingers of a second sheet comprising the second substrate.

5. The layered sensor of claim 1, wherein the first electrode comprises silver.

6. The layered sensor of claim 1, wherein the first substrate comprises a flexible piezoelectric material.

7. The layered sensor of claim 6, wherein the second substrate does not comprise the flexible piezoelectric material.

8. The layered sensor of claim 1, wherein the sleep characteristic is at least one of a heart rate, a breathing rate, a sleep duration, a snoring duration, a temperature, or a humidity level.

9. A flexible sleep monitor, comprising:
   an enclosure; and
   a layered sensor at least partially surrounded by the enclosure, and comprising:
      a substrate layer positioned within the enclosure, and comprising:
         a first substrate formed from a first material; and
         a second substrate positioned laterally adjacent to the first substrate and formed from a second material different from the first material; and
      a flexible layer positioned between the substrate layer and a portion of the enclosure, and comprising a third substrate, wherein:
      the substrate layer is formed by interdigitating first members of a first sheet section of a first sheet comprising the first substrate with second members of a second sheet section of a second sheet comprising the second substrate to form a combined sheet.

10. The flexible sleep monitor of claim 9, wherein forming the layered sensor further comprises:
    attaching the combined sheet to a third sheet to form a stack; and
    separating the stack into a first portion and one or more additional portions, the first portion including the first substrate, the second substrate, and the third substrate.

11. The flexible sleep monitor of claim 9, wherein:
    the layered sensor further comprises:
       a first electrode positioned on the first substrate; and
       a second electrode positioned on the second substrate; and
    the first electrode and the second electrode are configured to be electrically coupled to a processing unit configured to determine a sleep characteristic using a signal received from at least one of the first electrode or the second electrode.

12. The flexible sleep monitor of claim 9, wherein:
    the first material is a flexible piezoelectric material; and
    the second substrate does not comprise the flexible piezoelectric material.

13. A layered sensor, comprising:
    a first flexible layer;
    a second flexible layer that is substantially parallel to the first flexible layer;
    a substrate layer positioned between the first flexible layer and the second flexible layer, and comprising:
       a first substrate formed of a first material, and configured to generate electric charge in response to a force applied to the layered sensor; and
       a second substrate formed of a second material different from the first material and positioned laterally adjacent to the first substrate;
    a first electrode disposed on a first surface of the first substrate; and
    a second electrode disposed on a second surface of the first substrate, the second surface opposite the first surface, wherein:

the substrate layer is flexible; and
at least a portion of the first substrate has a curved shape extending parallel to the substrate layer.

14. The layered sensor of claim 13, wherein at least a portion of the first substrate has a serpentine shape within the substrate layer.

15. The layered sensor of claim 13, further comprising:
a differential sensor having a first input electrically connected to the first electrode and a second input electrically connected to the second electrode.

16. The layered sensor of claim 13, wherein the first electrode and the second electrode are configured to provide a differential signal to a processing unit configured to determine a sleep characteristic of a user using the differential signal.

17. The layered sensor of claim 13, wherein the first substrate is a PVDF substrate.

18. The layered sensor of claim 17, wherein the second substrate is a polyurethane substrate.

19. The layered sensor of claim 17, wherein the first electrode and the second electrode comprise silver.

20. The layered sensor of claim 13, wherein the first substrate comprises a flexible piezoelectric material.

21. The layered sensor of claim 20, wherein the second substrate does not comprise the flexible piezoelectric material.

* * * * *